US009925344B2

(12) United States Patent
Brereton et al.

(10) Patent No.: US 9,925,344 B2
(45) Date of Patent: Mar. 27, 2018

(54) AUTO-INJECTOR

(75) Inventors: Simon Francis Brereton, Cambridgeshire (GB); Thomas Kemp, Hertfordshire (GB); Rosie Burnell, Cambridgeshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 642 days.

(21) Appl. No.: 13/983,809

(22) PCT Filed: Feb. 16, 2012

(86) PCT No.: PCT/EP2012/052647
§ 371 (c)(1),
(2), (4) Date: Aug. 6, 2013

(87) PCT Pub. No.: WO2012/110578
PCT Pub. Date: Aug. 23, 2012

(65) Prior Publication Data
US 2013/0317430 A1 Nov. 28, 2013

(30) Foreign Application Priority Data
Feb. 18, 2011 (EP) .................................... 11155040

(51) Int. Cl.
*A61M 5/20* (2006.01)
*A61M 5/46* (2006.01)
(Continued)

(52) U.S. Cl.
CPC ................ *A61M 5/46* (2013.01); *A61M 5/20* (2013.01); *A61M 5/2033* (2013.01);
(Continued)

(58) Field of Classification Search
CPC .... A61M 5/20; A61M 5/2033; A61M 5/3157; A61M 2005/2013; A61M 5/1424;
(Continued)

(56) References Cited

U.S. PATENT DOCUMENTS 5,137,516 A * 8/1992 Rand ......................... A61J 1/00
604/136
5,320,609 A   6/1994 Haber
(Continued)

FOREIGN PATENT DOCUMENTS

CN        1901957     1/2007
CN      101264360     3/2008
(Continued)

OTHER PUBLICATIONS

International Search Report for Int. App. No. PCT/EP2012/052647, completed Apr. 25, 2012.
(Continued)

*Primary Examiner* — Bhisma Mehta
*Assistant Examiner* — James D Ponton
(74) *Attorney, Agent, or Firm* — Fish & Richardson P.C.

(57) ABSTRACT

An auto-injector for administering a dose of a liquid medicament (M) is present having a tubular chassis telescopable in a tubular case, a carrier subassembly comprising a tubular carrier slidably arranged relative to the chassis inside the case, where the carrier is adapted to contain a syringe with a hollow injection needle. The injector also has a drive spring and a plunger for forwarding load of the drive spring to a stopper of the syringe, wherein the syringe is lockable for joint axial translation with the carrier. A control spring is arranged around the carrier for translating the carrier in a proximal direction (P) for insertion of the needle through the chassis into an injection site.

18 Claims, 27 Drawing Sheets

(51) Int. Cl.
  *A61M 5/32* (2006.01)
  *A61M 5/315* (2006.01)
(52) U.S. Cl.
  CPC .......... *A61M 5/3157* (2013.01); *A61M 5/326* (2013.01); *A61M 2005/206* (2013.01); *A61M 2205/581* (2013.01); *A61M 2205/582* (2013.01)
(58) Field of Classification Search
  CPC .......... A61M 5/2429; A61M 2005/208; A61M 5/3137; A61M 25/0631; A61M 2005/206
  See application file for complete search history.

(56) References Cited

U.S. PATENT DOCUMENTS

| | | |
|---|---|---|
| 5,681,291 A | 10/1997 | Galli |
| 5,746,215 A | 5/1998 | Brunnherg et al. |
| 6,221,046 B1 | 4/2001 | Burroughs |
| 6,270,479 B1 | 8/2001 | Bergens et al. |
| 7,361,160 B2 | 4/2008 | Hommann |
| 7,407,494 B2 | 8/2008 | Bostrom |
| 7,442,185 B2 | 10/2008 | Amark et al. |
| 7,749,195 B2 | 7/2010 | Hommann |
| 7,758,550 B2 | 7/2010 | Bollenbach |
| 8,308,695 B2 | 11/2012 | Laiosa |
| 9,155,844 B2 | 10/2015 | Brereton et al. |
| 9,242,047 B2 | 1/2016 | Brereton et al. |
| 9,352,090 B2 | 5/2016 | Brereton |
| 2001/0005781 A1 | 6/2001 | Bergens |
| 2002/0009520 A1 | 1/2002 | Clayton et al. |
| 2002/0095120 A1 | 7/2002 | Larsen et al. |
| 2002/0123675 A1 | 9/2002 | Trautman et al. |
| 2002/0133122 A1 | 9/2002 | Giambattista |
| 2004/0097883 A1 | 5/2004 | Roe |
| 2005/0027255 A1 | 2/2005 | Lavi et al. |
| 2005/0101919 A1 | 5/2005 | Brunnberg et al. |
| 2005/0272551 A1 | 12/2005 | Oates |
| 2007/0005021 A1 | 1/2007 | Kohlbrenner et al. |
| 2007/0112310 A1 | 5/2007 | Lavi et al. |
| 2007/0197975 A1 | 8/2007 | Burren et al. |
| 2008/0009807 A1 | 1/2008 | Hommann |
| 2008/0015520 A1 | 1/2008 | Hommann et al. |
| 2008/0051713 A1 | 2/2008 | Kohlbrenner et al. |
| 2008/0210890 A1 | 9/2008 | Fago |
| 2008/0228143 A1 | 9/2008 | Stamp |
| 2008/0228147 A1 | 9/2008 | David-Hegerich et al. |
| 2008/0262438 A1 | 10/2008 | Bollenbach et al. |
| 2008/0262443 A1 | 10/2008 | Homman |
| 2009/0012479 A1 | 1/2009 | Moller et al. |
| 2009/0270804 A1 | 10/2009 | Mesa et al. |
| 2009/0312705 A1 | 12/2009 | Grunhut et al. |
| 2010/0137798 A1 | 6/2010 | Streit et al. |
| 2010/0137801 A1 | 6/2010 | Streit et al. |
| 2010/0191217 A1 | 7/2010 | Hommann |
| 2010/0268170 A1 | 10/2010 | Carrel et al. |
| 2010/0286612 A1 | 11/2010 | Cirillo et al. |
| 2010/0292653 A1 | 11/2010 | Maritan |
| 2010/0298780 A1 | 11/2010 | Laiosa |
| 2011/0077599 A1 | 3/2011 | Wozencroft |
| 2011/0218500 A1 | 9/2011 | Grunhut et al. |
| 2012/0116319 A1 | 5/2012 | Grunhut et al. |
| 2012/0209192 A1 | 8/2012 | Alexandersson |
| 2012/0310156 A1 | 12/2012 | Karlsson et al. |
| 2013/0310739 A1 | 11/2013 | Galbraith et al. |
| 2013/0310744 A1 | 11/2013 | Brereton et al. |
| 2013/0310745 A1 | 11/2013 | Latham et al. |
| 2013/0310757 A1 | 11/2013 | Brereton et al. |
| 2013/0317427 A1 | 11/2013 | Brereton |
| 2013/0317479 A1 | 11/2013 | Brereton |
| 2013/0324939 A1 | 12/2013 | Brereton et al. |

FOREIGN PATENT DOCUMENTS

| | | |
|---|---|---|
| DE | 102007013836 | 9/2008 |
| EP | 0693946 | 1/1996 |
| EP | 1932558 | 6/2008 |
| EP | 2675502 | 12/2013 |
| GB | 2469672 | 10/2010 |
| JP | 2007/500530 | 1/2007 |
| JP | 2007/504867 | 3/2007 |
| JP | 2008/528144 | 7/2007 |
| JP | 2008/229344 | 10/2008 |
| WO | WO 1996/032974 | 10/1996 |
| WO | WO 2000/024441 | 5/2000 |
| WO | WO 2000/035060 | 6/2000 |
| WO | WO 2004/108194 | 12/2004 |
| WO | WO 2005/097238 | 10/2005 |
| WO | WO 2009/062508 | 5/2009 |
| WO | WO 2009/095701 | 8/2009 |
| WO | 2010/035060 | 4/2010 |
| WO | WO 2010/035059 | 4/2010 |
| WO | WO 2012/000939 | 1/2012 |

OTHER PUBLICATIONS

International Preliminary Report on Patentability in International Application No. PCT/EP2012/052647, dated Aug. 21, 2013, 8 pages.
European Opposition in European Application No. 12703836.2-1660, dated Jan. 25, 2016, 29 pages.
European Search Report in European Application No. 11155039.8, dated Aug. 8, 2011, 5 pages.
Extended European Search Report in European Application No. 11155041.4, dated Aug. 30, 2011, 5 pages.
International Preliminary Report on Patentability in Application No. PCT/EP2012/052640, dated Aug. 21, 2013, 6 pages.
International Preliminary Report on Patentability in Application No. PCT/EP2012/052648, dated Aug. 21, 2013, 6 pages.
International Preliminary Report on Patentability in No. PCT/EP2012/052642, dated Aug. 21, 2013, 7 pages.
International Search Report and Written Opinion in Application No. GB0906973.3, dated Aug. 26, 2009, 2 pages.
International Search Report and Written Opinion in Application No. PCT/EP2012/052639, dated May 11, 2012, 9 pages.
International Search Report and Written Opinion in Application No. PCT/EP2012/052640, dated May 14, 2012, 8 pages.
International Search Report and Written Opinion in Application No. PCT/EP2012/052642, dated May 18, 2012, 11 pages.
International Search Report and Written Opinion in Application No. PCT/EP2012/052646, dated Nov. 5, 2012, 9 pages.
International Search Report and Written Opinion in Application No. PCT/EP2012/052648, dated May 18, 2012, 8 pages.
International Search Report and Written Opinion in Application No. PCT/EP2012/059758, dated Aug. 13, 2012, 12 pages.
International Search Report in Application No. PCT/EP2012/052643, dated Apr. 25, 2012, 3 pages.
International Search Report in Application No. PCT/EP2012/052652, dated May 10, 2012, 4 pages.
International Search Report in Application No. PCT/EP2012/052653, dated May 11, 2012, 3 pages.
International Search Report in Application No. PCT/SE99/01922, dated Mar. 28, 2000, 6 pages.
Japanese Office Action in Application No. 2013-553926, dated Jan. 5, 2016, 4 pages, English translation only.
Japanese Office Action in Application No. 2013-553927, dated Feb. 2, 2016, 5 pages.
Japanese Office Action in Application No. 2013-553931, dated Dec. 15, 2015, 5 pages, English translation only.
Japanese Office Action in Japanese Application No. 2013-553932, dated Dec. 4, 2015, 10 pages.
Japanese Office Action in Japanese Application No. 2013-553936, dated Dec. 22, 2015, 4 pages.
Office Action in U.S. Appl. No. 13/983,807, dated Dec. 24, 2015, 16 pages.
Office Action in U.S. Appl. No. 13/983,807, dated Jul. 28, 2015, 20 pages.
Office Action in U.S. Appl. No. 13/983,807, dated Oct. 21, 2016, 10 pages.

(56) References Cited

OTHER PUBLICATIONS

Office Action in U.S. Appl. No. 13/983,809, dated Mar. 28, 2016, 14 pages.
Office Action in U.S. Appl. No. 13/983,809, dated Sep. 27, 2016, 8 pages.
Office Action in U.S. Appl. No. 13/984,849, dated Jul. 26, 2016, 11 pages.
Office Action in U.S. Appl. No. 13/985,021, dated Jul. 26, 2016, 10 pages.
Office Action in U.S. Appl. No. 14/000,113, dated Mar. 19, 2015, 21 pages.
Office Action in U.S. Appl. No. 14/982,555, dated Dec. 21, 2016, 12 pages.
Russian Office Action in Application No. 2013/142343/14, dated Dec. 28, 2015, 6 pages, with English translation.
Russian Office Action in Application No. 2013/142356/14, dated Dec. 28, 2015, 6 pages, with English translation.
Russian Office Action in Application No. 2013/142356/14, dated Sep. 17, 2013, 6 pages.
Taiwan Search Report in Application No. 101105003, dated Nov. 5, 2015, 1 page.
Taiwan Search Report in Application No. 101105004, dated Nov. 3, 2015, 1 page.
Taiwan Search Report in Application No. 101105007, dated Oct. 22, 2015, 1 page.
Taiwan Search Report in Application No. 101105009, dated Oct. 31, 2015, 1 page.
Taiwan Search Report in Application No. 101105011, dated Oct. 31, 2015, 1 page.
International Search Report and Written Opinion in International Application No. PCT/EP2012/052653, dated May 11, 2012, 10 pages.
International Search Report and Written Opinion in International Application No. PCT/EP2012/052643, dated May 8, 2012, 12 pages.
Merriam-Webster Dictionary, 2015, Simple Definition, 1 page.

* cited by examiner

AUTO-INJECTOR

CROSS REFERENCE TO RELATED APPLICATIONS

The present application is a U.S. National Phase Application pursuant to 35 U.S.C. § 371 of International Application No. PCT/EP2012/052647 filed Feb. 16, 2012, which claims priority to European Patent Application No. 11155040.6 filed Feb. 18, 2011. The entire disclosure contents of these applications are herewith incorporated by reference into the present application.

TECHNICAL FIELD

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

High viscosity medicaments require high forces for expelling them through the relatively thin injection needle. To achieve these forces strong drive springs are needed. This can lead to a high impact felt by the user when inserting the needle into the skin and to high forces felt by the user when triggering the injection.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient. The term inwards refers to a radial direction pointing towards a longitudinal axis of the auto-injector whereas the term outwards refers to the opposite direction radially pointing away from the longitudinal axis.

According to the invention an auto-injector for administering a dose of a liquid medicament, comprises:

a tubular chassis telescopable in a tubular case, a carrier subassembly comprising a tubular carrier slidably arranged relative to the chassis inside the case, the carrier adapted to contain a syringe with a hollow injection needle, a drive spring and a plunger for forwarding load of the drive spring to a stopper of the syringe, wherein the syringe is lockable for joint axial translation with the carrier, a control spring arranged around the carrier for translating the carrier in a proximal direction for insertion of the needle through the chassis into an injection site.

The control spring is arranged to bias the case against the chassis in a distal direction so as to extend the chassis out of a proximal end of the case. An insertion depth of the needle is defined by the carrier abutting the chassis in a predefined position. The case is arranged to release or allow release of the control spring for needle insertion on translation of the case in the proximal direction relative to the chassis against the bias into an advanced position.

In the context of this specification the chassis is generally considered as being fixed in position so motion of other components is described relative to the chassis.

The needle insertion depth is defined by the carrier relative to the chassis not relative to the case, so if the user flinches or fails to hold the auto-injector hard against the injection site, only the case will move in the distal direction while the injection depth remains constant as the chassis is still being pressed against the injection site by the control spring. Maintaining the insertion depth is thought to avoid unnecessary pain to a patient as opposed to the needle being translated back and forth if the user flinches, e.g. due to tremor.

The carrier may be arranged to be translated in the distal direction for retracting the inserted needle when the case is moved in the distal direction relative to the chassis by a predefined distance. Retraction may be achieved by the control spring being released from the carrier at its proximal end and switched to the chassis or case instead and by the distal end of the control spring being switched from the case to the carrier. As long as the case motion does not exceed the predefined distance the case does not yet switch the control spring for needle retraction, i.e. the user may move the case below this distance without triggering refraction or altering the insertion depth.

The auto-injector may furthermore comprise:

a trigger button arranged distally or laterally in or on the case, a needle insertion control mechanism for coupling a proximal end of the control spring to either the carrier for advancing it for needle insertion or to the chassis for needle retraction depending on the relative axial position of the carrier and the chassis, a plunger release mechanism arranged for releasing the plunger for injection when the carrier has at least almost reached an injection depth during needle insertion, a detent mechanism arranged for coupling the chassis to the carrier for joint axial translation relative to the case, wherein the detent mechanism is arranged to decouple the chassis from the carrier upon actuation of the trigger button thus allowing the carrier to move relative to the chassis so as to cause the needle insertion control mechanism to switch the proximal end of the control spring to the carrier for needle insertion, a syringe retraction control mechanism arranged for coupling a distal end of the control spring to either the carrier for needle retraction or to the case otherwise.

The carrier subassembly with the integrated drive spring allows for employing a strong drive spring without any impact on the user when triggering the auto-injector or during needle insertion since these actions are achieved or opposed by the control spring which can be specified considerably weaker than the drive spring. This allows for delivering highly viscous medicaments.

There are a number of significant benefits of separating the functions between the drive spring and the control spring in this way. The auto-injector is always needle safe, i.e. the needle can be retracted before the injection is complete. The reliability of the auto-injector is improved as the components for needle advance and retraction are not loaded by the high impact of a freely expanding high force drive spring. The auto-injector is well suited to serve as a platform as the drive spring can be swapped to deliver different viscosity drugs without affecting the insertion or retraction functions. This is particularly advantageous for high viscosity fluids.

Releasing the drive spring upon the needle reaching the insertion or injection depth avoids a so called wet injection, i.e. medicament leaking out of the needle which is a problem in conventional art auto-injectors, where both needle insertion and injection are achieved by pushing on the stopper. The auto-injector solves the wet injection problem by the separate springs for translation of the carrier and for drug delivery.

The auto-injector has a particularly low part count compared to most conventional auto-injectors thus reducing manufacturing costs. The arrangement with separate control spring and drive spring for fluid injection allows for using one design for different viscosity liquids by just changing the drive spring, and for different volumes just by changing the length of the plunger. This is an advantage over conventional art designs where the main spring also powers needle insertion and/or retraction.

In an initial as delivered state of the auto-injector the proximal end of the control spring is coupled to the chassis by the needle insertion control mechanism while the distal end is coupled to the case by the syringe retraction control mechanism, release of the drive spring is prevented by the plunger release mechanism, decoupling of the chassis from the carrier is prevented by the detent mechanism.

In order to trigger an injection the auto-injector has to be pressed against an injection site, e.g. a patient's skin. A user, e.g. the patient or a caregiver, grabs the case with their whole hand and pushes the chassis protruding from the proximal end against the injection site.

When pushed against the injection site, the case translates in the proximal direction relative to the chassis against the force of the control spring. When the case has at least almost reached an advanced position the detent mechanism is unlocked thereby allowing translation of the carrier relative to the chassis.

The carrier can now be translated, preferably manually by depressing the trigger button forcing the carrier in the proximal direction. The carrier translates in the proximal direction relative to the case and to the chassis thereby switching the needle insertion control mechanism depending on the relative position of the carrier in the chassis so as to decouple the proximal end of the control spring from the chassis and couple it to the carrier, thereby releasing the control spring for advancing the carrier for needle insertion.

Alternatively the control spring could initially be coupled to the carrier by the needle insertion control mechanism so that the carrier would be immediately advanced when the detent mechanism is unlocked by translation of the case into the advanced position.

As the needle translated with the carrier subassembly at least almost reaches an injection depth the drive spring is released by the plunger release mechanism thereby allowing the drive spring to advance the plunger and the stopper for at least partially delivering the medicament. The release of the drive spring is preferably triggered by the carrier reaching a predefined relative position within the case.

If the auto-injector is removed from the injection site after the stopper has bottomed out in the syringe or mid injection, the case is translated in the distal direction under load of the control spring relative to the carrier subassembly.

As the case reaches a defined position relative to the carrier during that motion the proximal end of the control spring is decoupled from the carrier and coupled to the chassis by the needle insertion control mechanism. Furthermore the distal end of the control spring is decoupled from the trigger sleeve and coupled to the carrier by the syringe retraction control mechanism. As the control spring now pushes against the chassis in the proximal direction and against the carrier in the distal direction the carrier subassembly is retracted into the chassis into a needle safe position by the control spring.

According to one embodiment the needle insertion control mechanism may comprise a first collar biased by the control spring in the proximal direction, wherein at least one resilient beam is proximally arranged on the first collar, wherein respective recesses are arranged in the carrier and case, wherein a transversal extension of a head of the resilient beam is wider than a gap between the carrier and the chassis causing the head of the resilient beam to abut a distal face on the recess in the chassis while being prevented from deflecting in an inward direction by the carrier or to abut a distal face on the recess in the carrier while being prevented from deflecting in an outward direction by the chassis thereby forwarding load from the control spring to the carrier for needle insertion, wherein the resilient beam is arranged to be switched between the chassis and the carrier by ramped engagement of the head to the distal faces under load of the control spring depending on the relative longitudinal position between the chassis and the carrier. As the head of the resilient beam may be inwardly and outwardly ramped it may be referred to as an arrowhead.

The plunger release mechanism may comprise at least one resilient arm on the carrier arranged to be in a ramped engagement to the plunger so as to disengage them under load of the drive spring, wherein a peg protrudes from a distal end face of the trigger button in the proximal direction in a manner to support the resilient arm preventing disengagement of the carrier from the plunger and thus release of the drive spring when the carrier is in a distal position. The trigger button is arranged to remain in position relative to the case when the carrier is translated for advancing the needle. That means, the trigger button, initially coupled to the carrier, pushes the carrier in the proximal direction when depressed. As soon as the control spring takes over further advancing the carrier the trigger button may abut the case and decouple from the carrier, staying in position as the carrier moves on. Hence the resilient arm is pulled away from the peg thus allowing deflection of the resilient arm due to the ramped engagement under load of the drive spring for disengaging the plunger from the carrier and releasing the drive spring for drug delivery when the carrier has reached a predefined position during needle advancement.

The detent mechanism may be arranged to provide a resistive force which has to be overcome to advance the carrier in the proximal direction for needle insertion. Once the user applies a force on the trigger button which exceeds a pre-determined value the detent mechanism releases, initiating the injection cycle. If the pre-determined value is not overcome the detent mechanism pushes the carrier and trigger button back into their prior position. This ensures that the auto-injector is always in a defined state, either triggered or not triggered, not half triggered by the user hesitating.

The detent mechanism may also be arranged to provide a resistive force resisting translation of the carrier in the distal direction relative to the chassis for keeping the carrier in a defined position in a transitional state with both ends of the control spring decoupled from the carrier. This transitional state may be required for retracting the needle on removal from the injection site. As the carrier is biased against the injection site by the control spring before removal from the injection site it has to be decoupled from the proximal end of the control spring and coupled to the distal end for retraction. The sequencing of this switching is critical as retraction will fail if both ends of the control spring are attached to the carrier at the same time. This is overcome by separating the switching of the ends by a significant displacement of the case, which moves in the distal direction relative to the chassis on removal of the injection site under load of the control spring. As the switching of the distal end of the control spring to the carrier depends on the relative position of the case to the carrier the carrier has to be fixed in the transitional state which is achieved by the detent mechanism.

In one embodiment the detent mechanism comprises a resilient beam on the chassis and a rhomboid ramp member on the carrier, the resilient beam being essentially straight when relaxed and having a first beam head arranged to interact in a ramped engagement with a proximal fourth ramp or a distal fifth ramp on the rhomboid ramp member in such a manner that application of a translative force on the carrier relative to the chassis in the proximal direction with the first beam head engaged to the fourth ramp deflects the resilient beam in one transversal direction, e.g. outwards when a predetermined value of the translative force, at least depending on the resilience of the resilient beam, is overcome so as to allow the first beam head to travel along one transversal side of the rhomboid ramp member on continued relative translation of the components. The beam head may protrude transversally from the resilient beam in a manner to distort the resilient beam by lever action when pushed against the rhomboid ramp member thereby also defining the predetermined value of the translative force to be overcome by the carrier. Furthermore, the contacting faces of the first beam head and the rhomboid ramp member may have their friction adapted to define the required force by appropriately choosing their shape and material properties. The resilient beam is allowed to relax when the first beam head has reached the fifth ramp thereby engaging it in a manner that application of a translative force on the carrier in the distal direction deflects the resilient beam in the other transversal direction, e.g. inwards when a predetermined value of the translative force, at least depending on the resilience of the resilient beam, is overcome so as to allow the first beam head to travel along the other transversal side of the rhomboid ramp member on continued translation of the carrier. The first beam head may also be allowed to relax behind the fourth ramp at the end of this motion for preventing the carrier from being advanced again, e.g. when the auto-injector is being heavily shaken after use.

It goes without saying that the positions of the resilient beam on the chassis and the rhomboid ramp member on the carrier may be switched without altering the function of the detent mechanism.

When the auto-injector or the syringe is assembled a protective needle sheath may be attached to the needle for keeping the needle sterile and preventing both, damage to the needle during assembly and handling and access of a user to the needle for avoiding finger stick injuries. Removal of the protective needle sheath prior to an injection usually requires a relatively high force for pulling the protective needle sheath off the needle and needle hub in the proximal direction. In order to maintain pre injection needle safety and prevent exposure of the needle translation of the syringe in the proximal direction due to this force has to be avoided. For this purpose the case may be arranged to lock the detent mechanism prior to being translated in the proximal direction relative to the chassis when the chassis is being pressed against the injection site so as to avoid translation of the carrier. This may be achieved by a rib in the case preventing deflection of the resilient beam of the detent mechanism by supporting it outwardly. Translation of the case is translated into the advanced position in the proximal direction on contact to the injection site is arranged to unlock the detent mechanism rendering it operable. This may be achieved by the rib being moved with the case so as to no longer outwardly supporting the resilient beam of the detent mechanism. In order to ensure that the case is not moved in the proximal direction unlocking the detent mechanism before the protective needle sheath is removed a cap may be attached to the proximal end of the case so as to make the chassis inaccessible before the cap is removed. The cap preferably engages the protective needle sheath by means of a barb in a manner to remove the protective needle sheath when the cap is being pulled off the auto-injector. In order to facilitate removal of the cap it may have a profiled surface mating with a surface on the case so that the cap is pulled off when rotated. The barb may be connected to the cap in a manner allowing them to rotate independently so as to avoid torque on the protective needle sheath when the cap is rotated in order not to distort the needle inside the protective needle sheath.

The distally arranged trigger button may be at least initially coupled to the carrier, wherein the case is arranged to abut the trigger button in the initial state preventing depression of the trigger button. On translation of the case into the advanced position when the chassis is being pressed against the injection site the trigger button remains coupled to the carrier thus emerging from the case which has been moved relative to the chassis, carrier and trigger button so as to allow depression of the trigger button for starting an injection cycle. Thus a sequence of operation is defined for the auto-injector to be actuated, first pressing it against the injection site and then to push the trigger button. This reduces the risk of finger stick injuries particularly if the user were to be confused which end of the auto-injector to apply against their skin. Without a sequence the user would risk inserting the needle into their thumb which is significantly less probable with the forced sequence.

The syringe retraction control mechanism may comprise a second collar bearing against the distal end of the control spring and having a resilient proximal beam with a second beam head having an inward boss. The second beam head is arranged to be in a ramped engagement with a second case detent in the case in a manner ramping the second beam head in the inward direction under load of the control spring in the distal direction. The inward boss is arranged to inwardly abut the carrier for preventing inward deflection of the second beam head and keep the second collar locked to the case. A third recess is arranged in the carrier for allowing the inward boss to be inwardly deflected on translation of the case in the distal direction relative to the carrier on removal of the auto-injector from the injection site.

In an alternative embodiment the first collar and/or the second collar may also be threaded to one of the components which they are intended to couple to the control spring wherein the case would be arranged to prevent the threads from decoupling in some relative longitudinal positions while allowing the collar to rotate out of the threaded engagement in other relative longitudinal positions so as to allow the collars to switch to the respective other component to be coupled to the control spring.

In an alternative embodiment the trigger button may be arranged distally, wherein the case is arranged as a wrap-over sleeve trigger having a closed distal end face covering the trigger button. In an initial state a clearance is provided between the distal end face of the sleeve trigger and the trigger button allowing for some travel of the sleeve trigger against the bias of the control spring in the proximal direction in a first phase before abutting the trigger button. As soon as the sleeve trigger has contacted the trigger button the trigger button is pushed by the sleeve trigger on further translation in a second phase. This embodiment allows for keeping the majority of the components of the auto-injector while only the described features need modification allowing to customize a platform device to particular requirements. An auto-injector with a sleeve trigger is particularly well suited for people with dexterity problems since, as opposed to conventional art auto-injectors, triggering does not require operation of small buttons by single fingers. Instead, the whole hand is used.

Retraction of the needle requires the user to lift the auto-injector far enough from the injection site to allow the case or sleeve trigger to translate back in the distal direction to switch the control spring. As it may be difficult for the user to know if the injection is finished or not a releasable noise component may be provided, capable of, upon release, generating an audible and/or tactile feedback to the user, wherein the noise component is arranged to be released when the plunger reaches a position relative to the syringe in which the stopper is located in proximity of a proximal end of the syringe, i.e. when the injection is at least almost finished. The released noise component then impacts on a housing component, such as the case, sleeve trigger or trigger button indicating the end of the injection. Impacting a directly accessible component allows for high perceptibility of the noise and direct access to the user's hand or finger for generating the tactile feedback. Preferably the noise component may impact the trigger button which may be shaped as a drum for providing a loud noise.

The auto-injector may be operated by a number of key mechanical operations:

The case is advanced relative to the chassis compressing the control spring giving the user the impression of depressing a skin interlock sleeve. All other components remain in the same place during case advance resulting in the trigger button appearing from the distal end of the case.

The user pushes the trigger button which can now be operated. Button depression directly moves the carrier and hence the drive sub-assembly in the proximal direction a set distance until the control spring takes over via the first collar and inserts the needle into the injection site.

The trigger button stops on the distal end of the case as the carrier continues translating in the proximal direction. The motion of the carrier relative to the trigger button is used to release the drive spring just before full insertion depth is reached, e.g. by pulling a peg on the trigger button out of the carrier thus allowing the plunger to move. The drive spring drives the plunger down the syringe barrel expelling the medicament.

A noise mechanism is released when the plunger is near the end of travel shortly before the stopper bottoms out in the syringe, indicating the end of injection to the user.

The needle remains fully inserted until the user moves the case back a set distance at which point the second collar decouples from the case and couples to the carrier while the first collar decouples from the carrier and couples to the chassis thus allowing the control spring to retract the carrier and hence the needle.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
herein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drive spring and control spring may be compression springs. However, they may likewise be any kind of stored energy means such as torsion springs, gas springs etc.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

A ramped engagement in the terminology of this specification is an engagement between two components with at least one of them having a ramp for engaging the other component in such a manner that one of the components is flexed aside when the components are axially pushed against each other provided this component is not prevented from flexing aside.

Figure 1A:
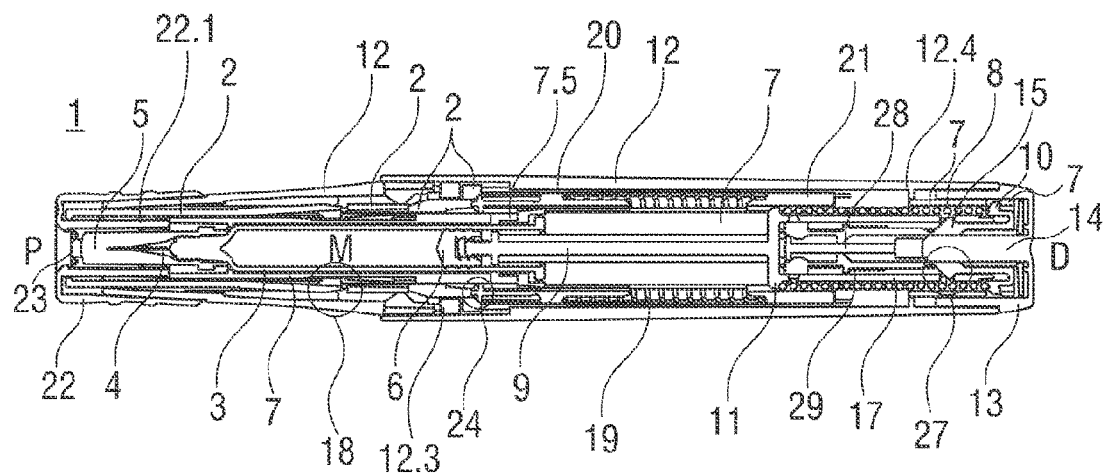
FIGS. 1A and 1B show two longitudinal sections of an auto-injector in different section planes in a state prior to use.
Figure 1B:
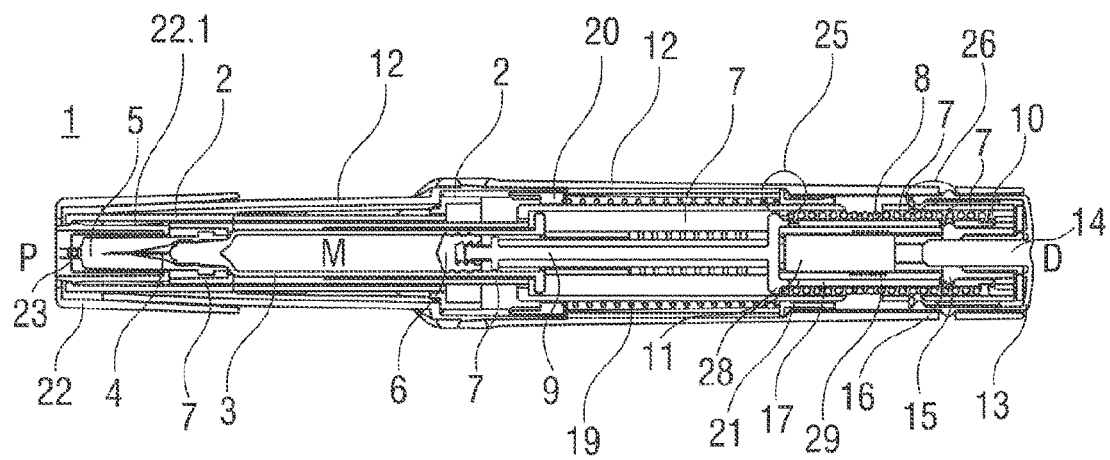

FIGS. 1*a* and 1*b* show two longitudinal sections of an auto-injector 1 in different section planes, the different section planes approximately 90° rotated to each other, wherein the auto-injector 1 is in an initial state prior to starting an injection. The auto-injector 1 comprises a chassis 2. In the following the chassis 2 is generally considered as being fixed in position so motion of other components is described relative to the chassis 2. A syringe 3, e.g. a Hypak syringe, with a hollow injection needle 4 is arranged in a proximal part of the auto-injector 1. When the auto-injector 1 or the syringe 3 is assembled a protective needle sheath 5 is attached to the needle 4. A stopper 6 is arranged for sealing the syringe 3 distally and for displacing a liquid medicament M through the hollow needle 4. The syringe 3 is held in a tubular carrier 7 and supported at its proximal end therein. The carrier 7 is slidably arranged in the chassis 2.

A drive spring 8 in the shape of a compression spring is arranged in a distal part of the carrier 7. A plunger 9 serves for forwarding the force of the drive spring 8 to the stopper 6.

The drive spring 8 is loaded between a distal carrier end face 10 of the carrier 7 and a thrust face 11 arranged distally on the plunger 9.

The carrier 7 is a key element housing the syringe 3, the drive spring 8 and the plunger 9, which are the components required to eject the medicament M from the syringe 3. These components can therefore be referred to as a drive sub-assembly.

Figure 15A:
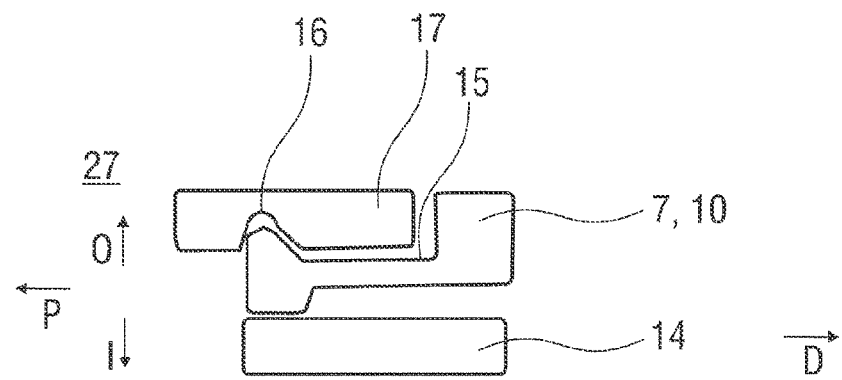
FIGS. 15A, 15B and 15C show schematic views of a plunger release mechanism in three different states.

The chassis 2 and the carrier 7 are arranged within a tubular case 12. A trigger button 13 is arranged at a distal end of the case 12. In a plunger release mechanism 27 a peg 14 protrudes from a distal end face of the trigger button 13 in the proximal direction P between two resilient arms 15 originating from the distal carrier end face 10 thus preventing them from flexing towards each other in an initial state A illustrated in FIG. 15A. In FIG. 15A only one of the resilient arms 15 is shown to illustrate the principle. Outwardly the resilient arms 15 are caught in respective first recesses 16 in a distal plunger sleeve 17 attached distally to the thrust face 11 and arranged inside the drive spring 8. The engagement of the resilient arms 15 in the first recesses 16 prevents axial translation of the plunger 9 relative to the carrier 7. The resilient arms 15 are ramped in a manner to flex them inwards on relative motion between the plunger 9 and the carrier 7 under load of the drive spring 8, which is prevented by the peg 14 in the initial state A.

The carrier 7 is locked to the chassis 2 for preventing relative translation by a detent mechanism 18 illustrated in more detail in FIGS. 11A to 11D.

Figure 16A:
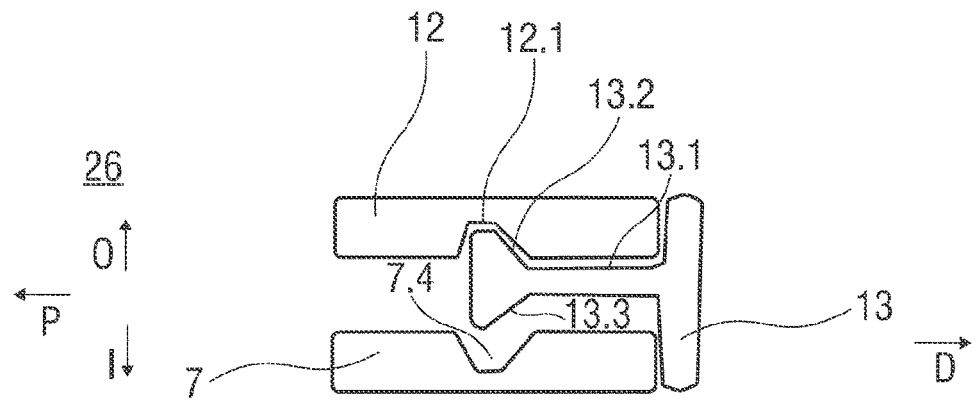
FIGS. 16A, 16B and 16C show schematic views of a button release mechanism in three different states.
Figure 16B:
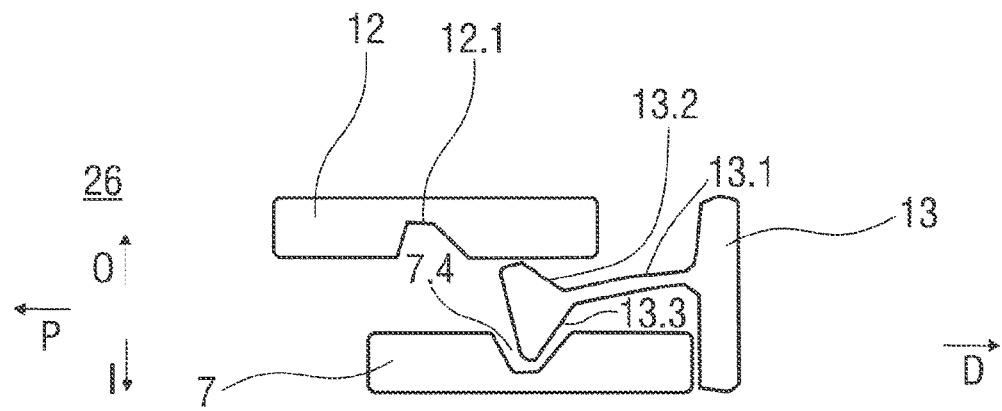

The trigger button 13 is initially engaged to the case 12 by a button release mechanism 26 and cannot be depressed. The button release mechanism 26 is illustrated in detail in FIGS. 16A to 16C. Referring now to FIG. 16A the button release mechanism 26 comprises a resilient proximal beam 13.1 on the trigger button 13, the proximal beam 13.1 having an outward first ramp 13.2 and an inward second ramp 13.3. In an initial state A illustrated in FIG. 16A the outward first ramp 13.2 is engaged in a ramped first case detent 12.1 preventing the trigger button 13 from moving out of the distal end D. The trigger button 13 proximally abuts both the case 12 and the carrier 7 hence being prevented from being depressed in the proximal direction P.

Referring again to FIGS. 1A and 1B a control spring 19 in the shape of another compression spring is arranged around the carrier 7 and acts between a proximal first collar 20 and a distal second collar 21. The control spring 19 is used to move the carrier 7 and hence the drive sub-assembly in the proximal direction P for needle insertion or in the distal direction D for needle retraction.

In the state as delivered as shown in FIGS. 1a and 1b a cap 22 is attached to the proximal end of the case 12 and the protective needle sheath 5 is still in place over the needle 4 and the needle hub. An inner sleeve 22.1 of the cap 22 is arranged inside the chassis 2 and over the protective needle sheath 5. In the inner sleeve 22.1 a barb 23 is attached. The barb 23 is engaged to the protective needle sheath 5 for joint axial translation.

Figure 2A:
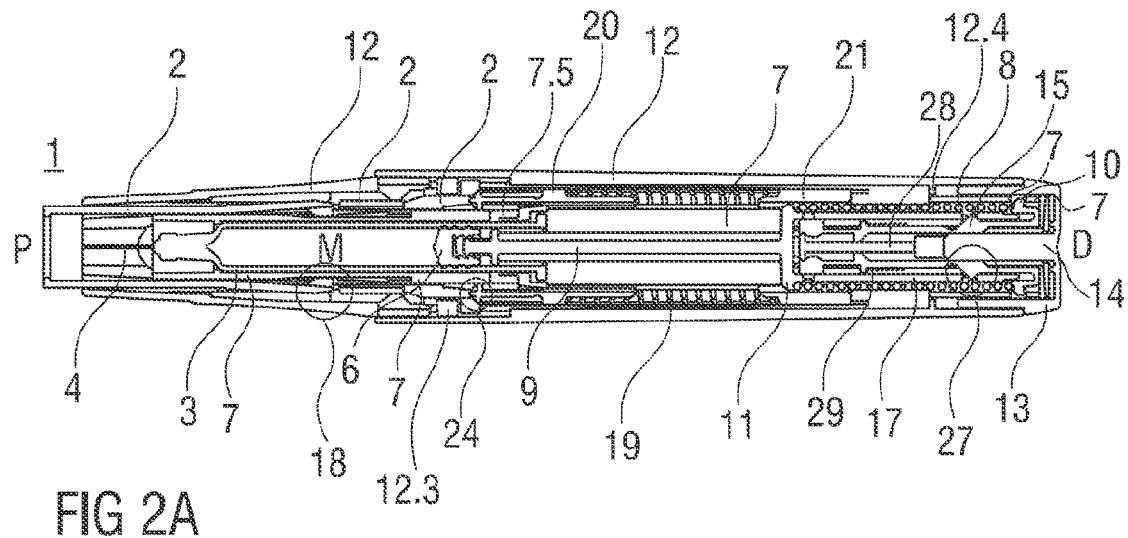
FIGS. 2A and 2B show two longitudinal sections of the auto-injector after removal of a cap and a protective needle sheath.
Figure 2B:
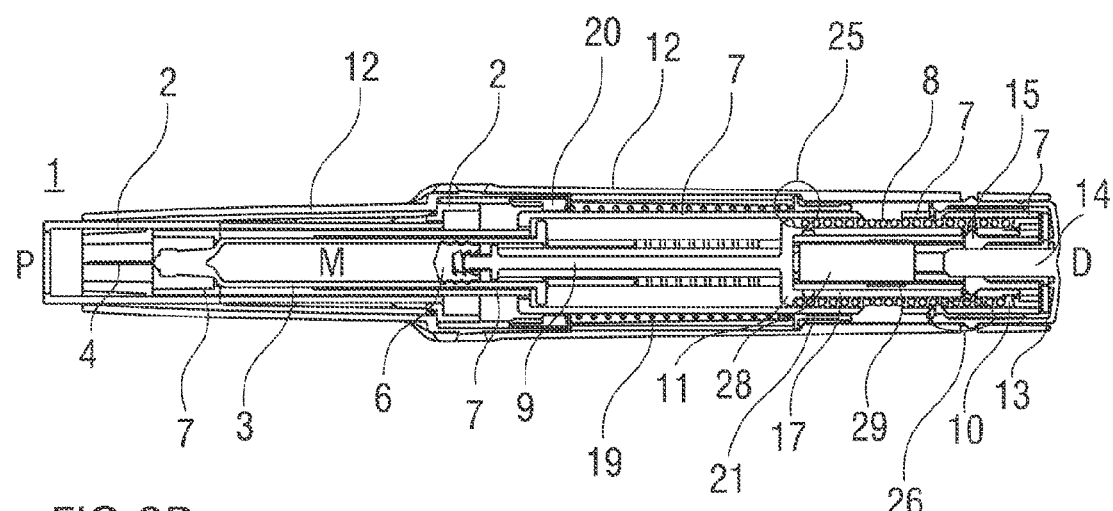
Figure 11A:
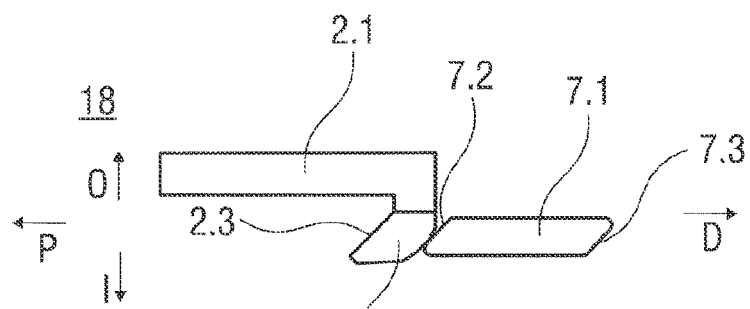
FIGS. 11A, 11B, 11C and 11D show schematic views of a detent mechanism for controlling movement of a carrier relative to a chassis of the auto-injector in four different states.

A sequence of operation of the auto-injector 1 is as follows:

A user pulls the cap 22 from the proximal end of the case 12. The barb 23 joins the protective needle sheath 5 to the cap 22. Hence, the protective needle sheath 5 is also removed on removal of the cap 22. FIGS. 2a and 2b show the auto-injector 1 with the cap 22 and needle sheath 5 removed. The carrier 7 and syringe 3 are prevented from moving in the proximal direction P by the detent mechanism 18 being in a state A as in FIG. 11A. Referring now to FIG. 11A, the detent mechanism 18 comprises a resilient beam 2.1 on the chassis 2 with an inwardly protruding first beam head 2.2. The first beam head 2.2 has a proximal third ramp 2.3. The detent mechanism 18 further comprises a rhomboid ramp member 7.1 on the carrier 7 having a proximal fourth ramp 7.2 and a distal fifth ramp 7.3. In state A a rounded off distal side of the first beam head 2.2 abuts the ramp member 7.1 in the distal direction D resisting movement of the carrier 7 in the proximal direction P relative to the chassis 2. A rib on the case 12 is provided for preventing outward deflection of the resilient beam 2.1 thereby also preventing motion of the carrier 7 relative to the chassis 2.

Figure 3A:
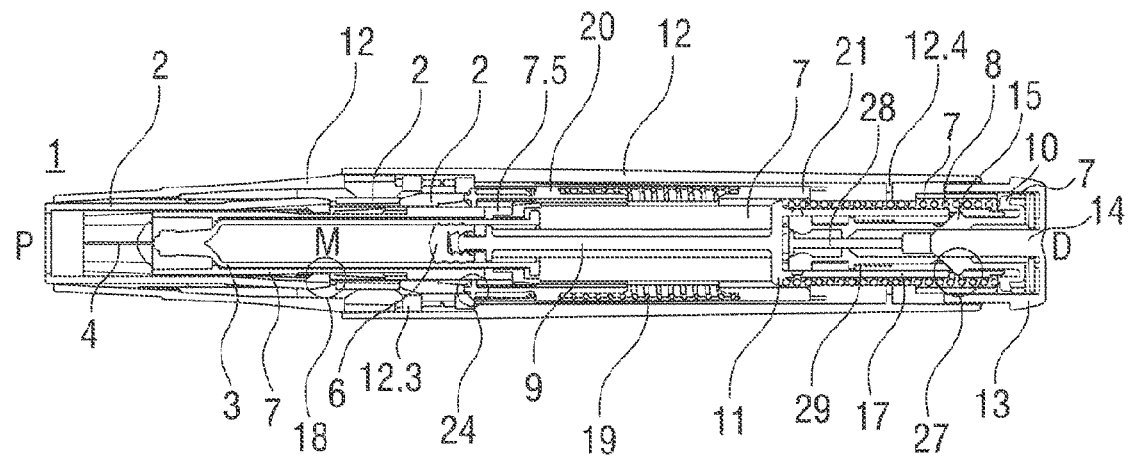
FIGS. 3A and 3B show two longitudinal sections of the auto-injector with a proximal end pressed against an injection site.
Figure 3B:
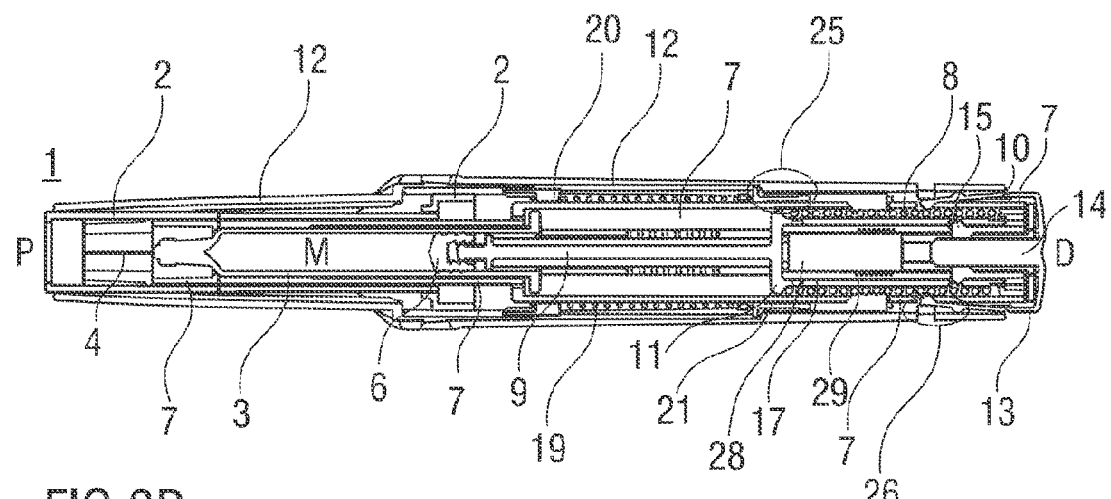
Figure 12A:
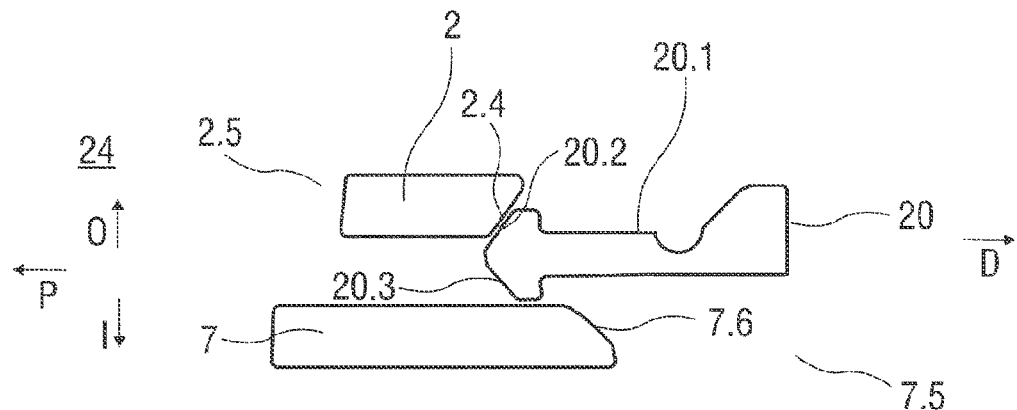
FIGS. 12A, 12B, 12C, 12D, 12E and 12F show schematic views of a needle insertion control mechanism for controlling movement of a first collar in six different states.

Referring again to FIGS. 2A and 2B the user grabs the case 12 and places the chassis 2 protruding from the case 12 at the proximal end P against an injection site, e.g. a patient's skin. As the auto-injector 1 is pressed against the injection site the case 12 translates in the proximal direction P relative to the chassis 2 into an advanced position as illustrated in FIGS. 3A and 3B. The second collar 21 is locked to the case 12 and is moved with the case 12 relative to the chassis 2 and relative to nearly all other components of the auto-injector 1 thus slightly compressing the control spring 19 against the first collar 20 which is prevented from moving in the proximal direction P by the chassis 2 due to a needle insertion control mechanism 24 being in a state A illustrated in detail in FIG. 12A. Referring now to FIG. 12A, a resilient member in the shape of an arrowhead 20.1 is proximally arranged on the first collar 20. The first collar 20 with the arrowhead 20.1 is being forced in the proximal direction P under load of the compressed control spring 19. An outward sixth ramp 20.2 on the arrowhead 20.1 interacts with a second distal seventh ramp 2.4 on the chassis 2 ramping the arrowhead 20.1 in an inward direction I which is prevented by the arrowhead 20.1 inwardly abutting the carrier 7. Hence, the first collar 20 cannot translate in the proximal direction P.

Figure 13A:
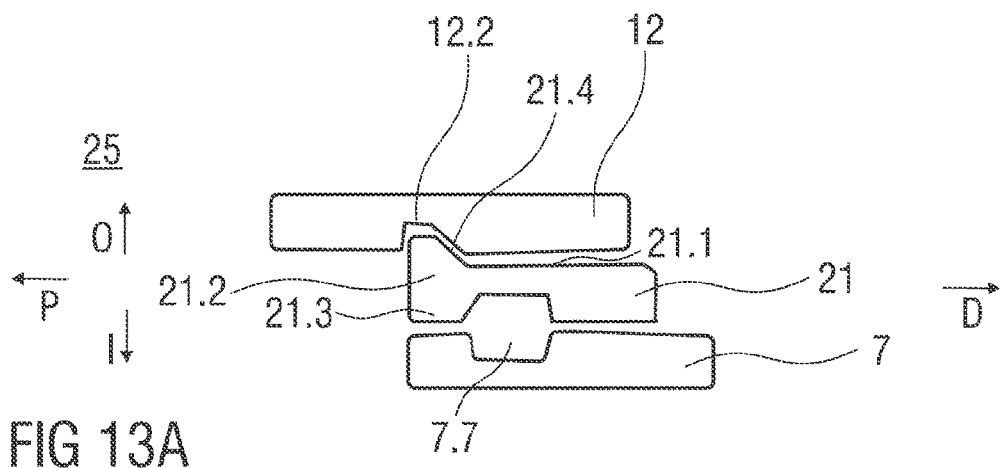
FIGS. 13A, 13B and 13C show schematic views of a syringe retraction control mechanism in three different states

Referring again to FIGS. 3A and 3B the second collar 21 is locked to the case due to a syringe refraction control mechanism 25 being in a state A illustrated in detail in FIG. 13A. Referring now to FIG. 13A, the syringe retraction control mechanism 25 comprises a resilient proximal beam 21.1 on the second collar 21, the proximal beam 21.1 having a second beam head 21.2 having an inward boss 21.3 and a distal outward eighth ramp 21.4. The distal outward eighth ramp 21.4 is engaged in a ramped second case detent 12.2 in a manner ramping the second beam head 21.1 in the inward direction I with the second collar 21 under load of the control spring 19 in the distal direction D which is prevented by the inward boss 21.3 inwardly abutting the carrier 7.

Referring again to FIGS. 3A and 3B, if the user was to move the case 12 away from the injection site, the control spring 19 expands returning the auto-injector 1 to the initial condition after removal of the cap 22 as illustrated in FIGS. 2A and 2B.

In the state as in FIGS. 3A and 3B the carrier 7 continues to be prevented from moving in the proximal direction P by the detent mechanism 18, however with the case 12 in its advanced position the detent mechanism 18 is unlocked as the rib on the case 12 has also moved and no longer prevents outward deflection of the resilient beam 2.1. Movement of the case 12 relative to the carrier 7, which is locked to the chassis 2 by the detent mechanism 18, causes the button release mechanism 26 to switch to a state B illustrated in FIG. 16B. The trigger button 13 cannot translate with the case 12 in the proximal direction P as it is abutted against the carrier 7. The ramp on the first case detent 12.1 interacts with the outward first ramp 13.2 on the proximal beam 13.1 on the trigger button 13 deflecting the proximal beam 13.1 in the inward direction I thus engaging the inward second ramp 13.3 on the proximal beam 13.1 in a ramped carrier detent 7.4 arranged in the carrier 7. As the case 12 is translated further in the proximal direction P it supports the proximal beam 13.1 outwardly thus locking the trigger button 13 to the carrier 7. The trigger button 13 now protrudes from the distal end D of the chassis 12 and is ready to be pressed.

Figure 11B:
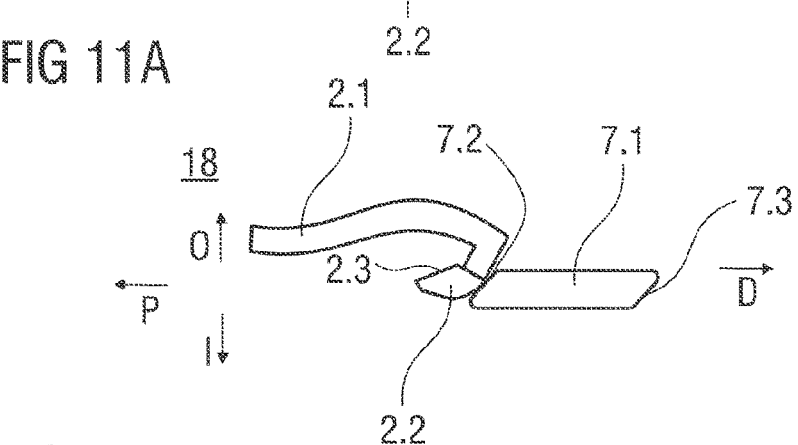
Figure 11C:
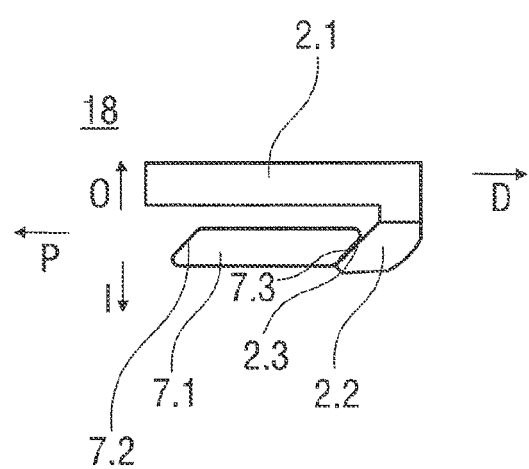

In the state as in FIGS. 3A and 3B the user depresses the trigger button 13 in the proximal direction P. As the trigger button 13 abuts against the carrier 7 the carrier 7 is pushing in the proximal direction P against the chassis 2, the carrier 7 and the chassis 2 interacting in the detent mechanism 18. The force exerted by the user pressing the trigger button 13 is resolved through the chassis 2 onto the injection site, not between the trigger button 13 and the case 12. The detent mechanism 18 provides a resistive force when the user pushes the trigger button 13. Once the user applies a force which exceeds a pre-determined value the detent mechanism 18 releases, initiating the injection cycle. Referring now to FIG. 11B showing the detent mechanism 18 in a state B, the resilient beam 2.1 on the chassis 2 begins to bow under load from the rhomboid ramp member 7.1 on the carrier 7, storing elastic energy. Despite the proximal fourth ramp 7.2 on the ramp member 7.1 friction between the contacting faces of the first beam head 2.2 and the proximal fourth ramp 7.2 prevents movement of the first beam head 2.2 in the outward direction O until the straightening force in the resiliently deformed beam 2.1 is sufficiently large to overcome it. At this point the resilient beam 2.1 is deflected in the outward direction O moving out of the way of the carrier 7 thus allowing the carrier 7 to translate in the proximal direction P. When the carrier 7 travels sufficiently far in the proximal direction P the rhomboid ramp member 7.1 on the carrier 7 passes under the first beam head 2.2 thus allowing it to relax and move back in the inward direction I distally behind the rhomboid ramp member 7.1 in a state C illustrated in FIG. 11C at the same time constraining translation of the carrier 7 in the distal direction D relative to the chassis 2.

Figure 12B:
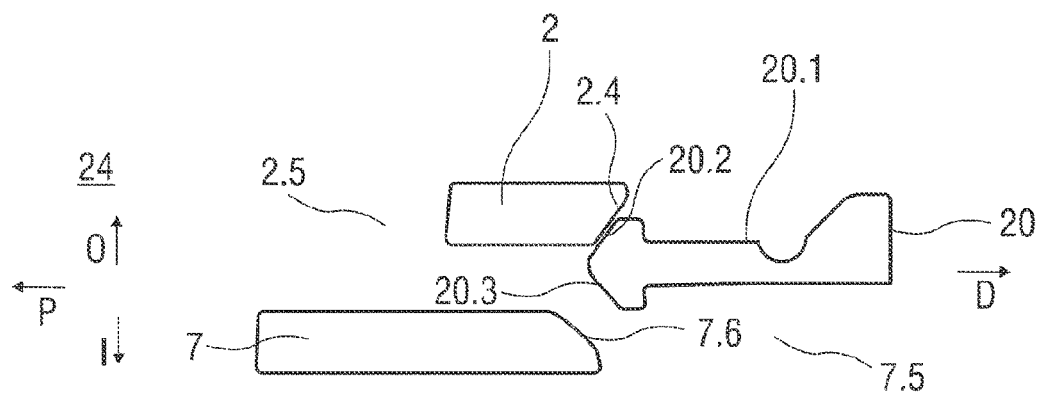
Figure 12C:
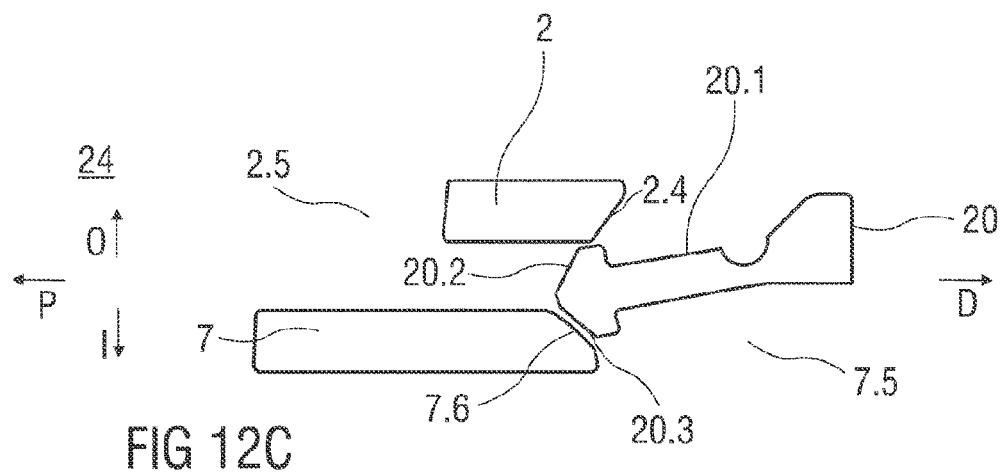

Once the carrier 7 slides far enough in the proximal direction P relative to the first collar 20 the needle insertion control mechanism 24 is switched to a state B as illustrated in FIG. 12B. In FIG. 12B the carrier 7 has been translated in the proximal direction P in such a manner that the arrowhead 20.1 on the first collar 20 is no longer inwardly supported. This may be achieved by a second recess 7.5 in the carrier 7. The arrowhead 20.1 is now deflected in the inward direction I into the second recess 7.5 under load of the control spring 19 arriving at a state C as illustrated in FIG. 12C. The first collar 20 is now decoupled from the chassis 2. Instead, the arrowhead 20.1 couples the first collar 20 to the carrier 7 by an inward ninth ramp 20.3 engaging a distal tenth ramp 7.6 on the carrier 7 at the proximal end of the second recess 7.5. Hence, the control spring 19 continues moving the carrier 7 in the proximal direction P from this point. Whilst the user advances the needle 4 by a proportion of its travel, the control spring 19 takes over insertion before the needle 4 protrudes from the proximal end P. Therefore the user experience is that of pressing a button, rather than manually inserting a needle.

The detent mechanism 18 relies on the user applying a force rather than a displacement. Once the force applied exceeds the force required to switch the detent the user will push the trigger button 13 fully, ensuring that the first collar 20 will always switch. If the user fails to pass the detent, the trigger button 13 returns to its unused state ready for use as illustrated in FIGS. 3A and 3B. This feature avoids the auto-injector 1 arriving in an undefined state.

Figure 4A:
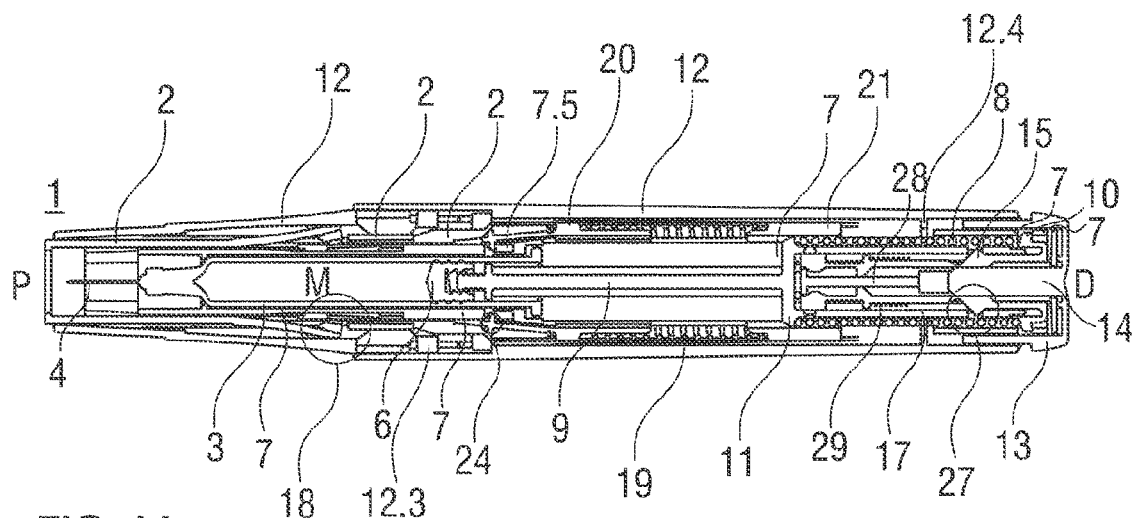
FIGS. 4A and 4B show two longitudinal sections of the auto-injector with a trigger button depressed.
Figure 4B:
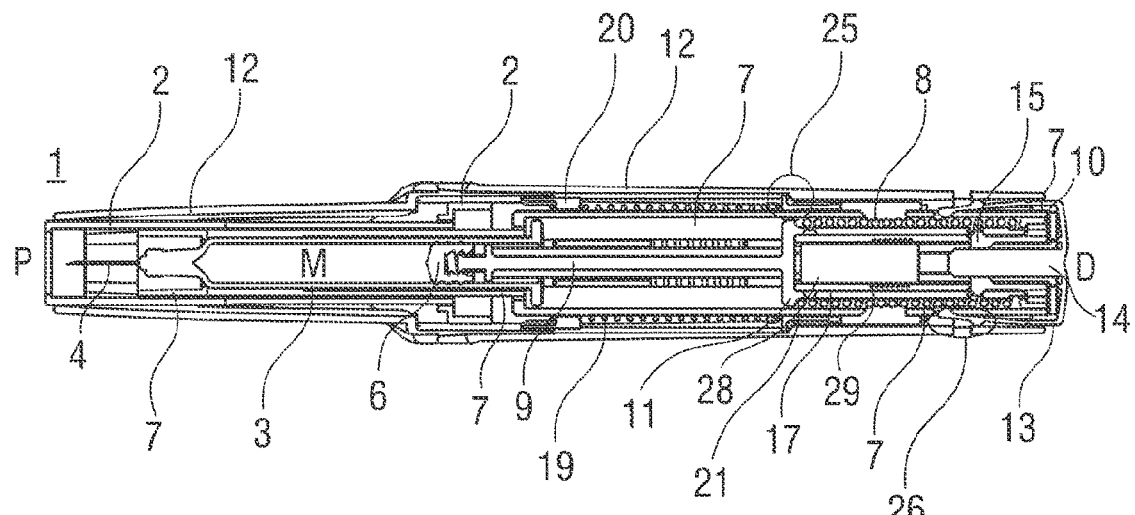

FIGS. 4A and 4B show the auto-injector 1 with the trigger button 13 depressed sufficiently for the control spring 19 to couple on to the carrier 7 and continue moving the carrier 7 forwards, but not yet abutting the case 12.

The carrier 7 coupled to the first collar 20 is translated in the proximal direction P driven by the control spring 19. As the syringe 3 is arranged for joint axial translation with the carrier 3 the syringe 3 and needle 4 are also translated resulting in the needle 4 protruding from the proximal end P and being inserted into the injection site. The trigger button 13 returns to its initial position relative to the case 12 and latches back to the case 12 from the carrier 7 as in state A in FIG. 16 A. The carrier 7 translates further in the proximal direction P preventing inward deflection of the proximal beam 13.1 so the outward first ramp 13.2 cannot disengage from the first case detent 12.1.

Figure 5A:
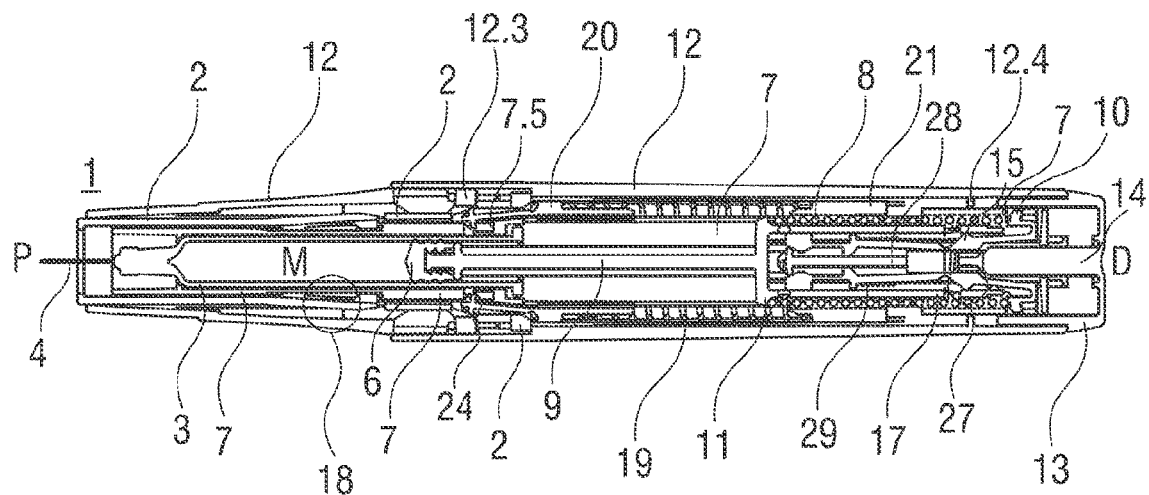
FIGS. 5A and 5B show two longitudinal sections of the auto-injector during needle insertion into the injection site.
Figure 5B:
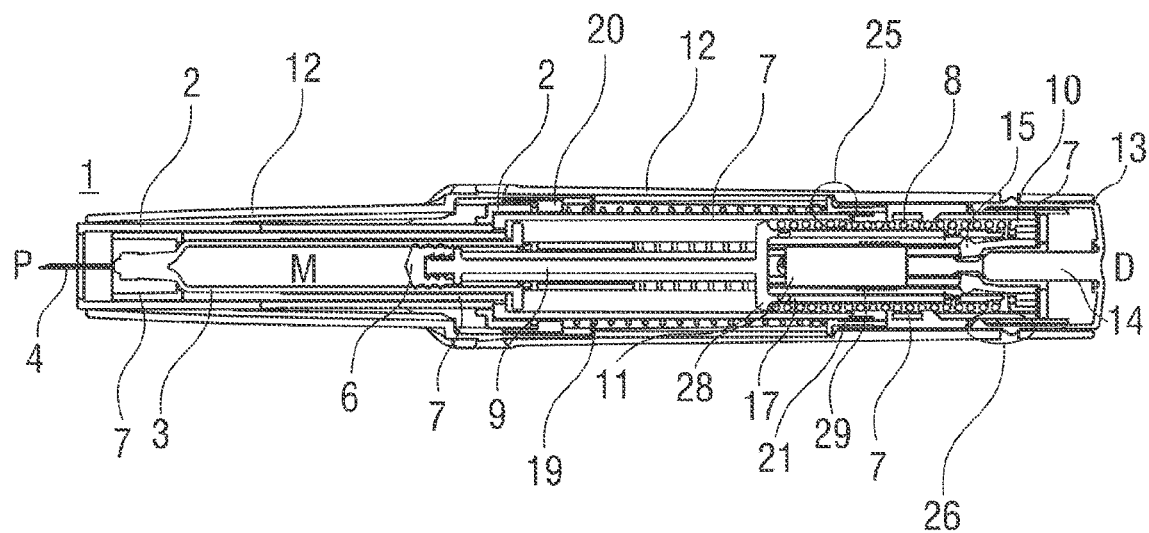
Figure 15B:
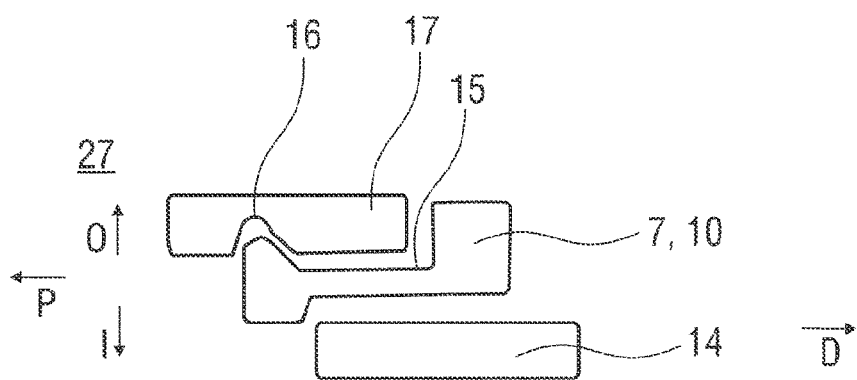
Figure 15C:
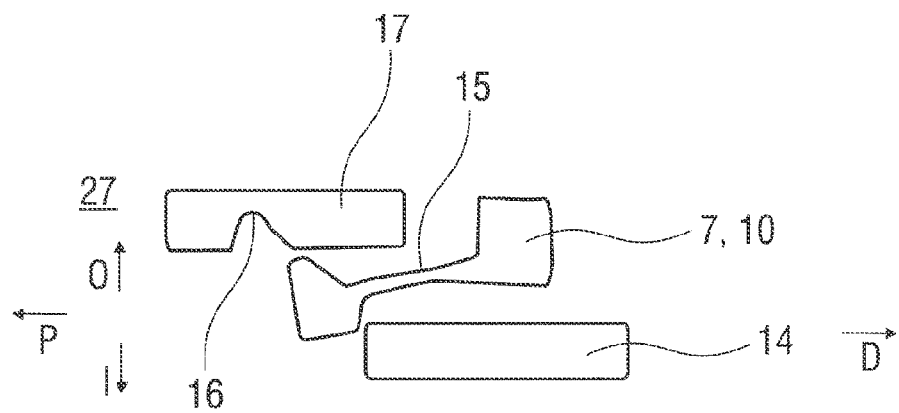

Immediately prior to the needle 4 reaching full insertion depth as illustrated in FIGS. 5A and 5B the peg 14 on the trigger button 13 is completely pulled out from between the resilient arms 15 on the carrier 7. Hence, the plunger release mechanism 27 arrives in a state B shown in FIG. 15B with the resilient arms 15 no longer inwardly supported by the peg 14. Due to the ramped engagement of the resilient arms 15 in the first recess 16 they are deflected in the inward direction I under load of the drive spring 8 arriving in a state B illustrated in FIG. 15C. Hence, the plunger 9 is released from the carrier 7 and driven in the proximal direction P by the drive spring 8, ready to inject the medicament M. The force to pull the peg 14 out from between the resilient arms 15 is provided by the control spring 19 while the force required to deflect the resilient arms 15 out of engagement to the plunger 9 is provided by the drive spring 8.

Figure 12D:
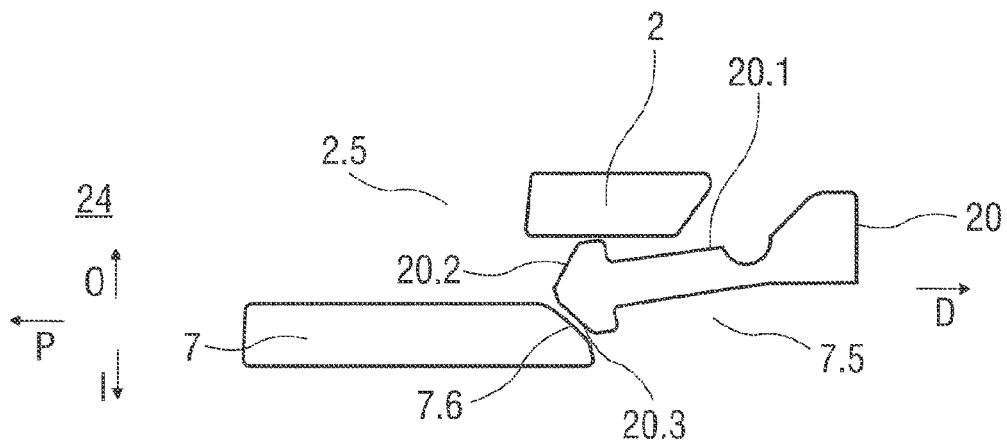

While the plunger 9 moves and closes a gap to the stopper 6 the movement of the carrier 7 in the proximal direction P is completed by the control spring 19 pushing the first collar 20. As the carrier 7 moves with respect to the chassis 2 during needle insertion the needle insertion mechanism 24 arrives in a state D illustrated in FIG. 12D. The arrowhead 20.1 has moved with the carrier 7 and is still kept inwardly deflected by the chassis 2 thus preventing the first collar 20 from disengaging the carrier 7. The arrowhead 20.1 must be able to deflect in the outward direction O to allow retraction which will be discussed below. In order to allow outward deflection the arrowhead 20.1 travels proximally beyond the part of the chassis 2 shown in FIGS. 12A to 12F next to an aperture 2.5 in the chassis 2. However, as long as the case 12 is being kept pressed against the injection site and not allowed to return in the distal direction D beyond a pre-defined distance under load of the control spring 19 the arrowhead 20.1 will be kept from deflecting in the outward direction O by a first rib 12.3 on the case 12 (not illustrated in FIGS. 12A to F, see FIGS. 5A to 8A) during about the second half of its motion for needle insertion.

Figure 6A:
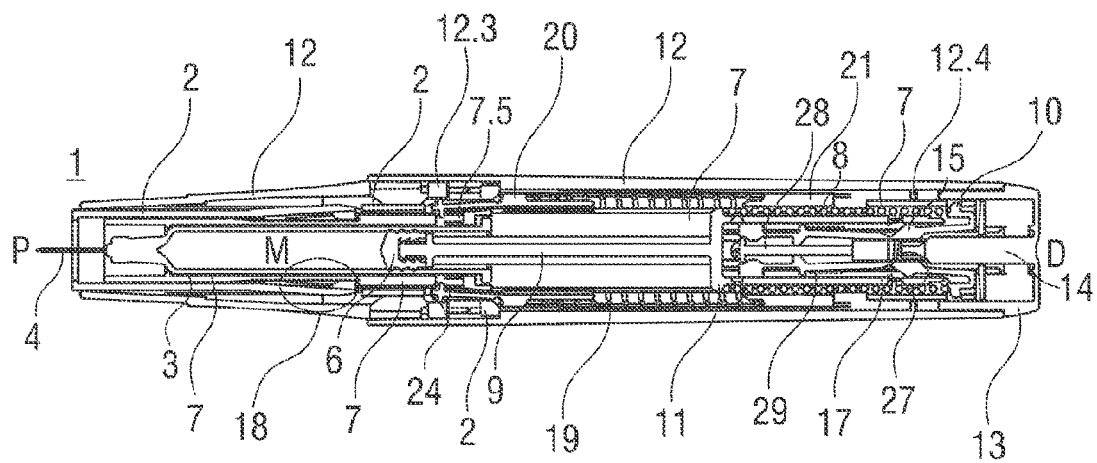
FIGS. 6A and 6B show two longitudinal sections of the auto-injector with the needle fully inserted.
Figure 6B:
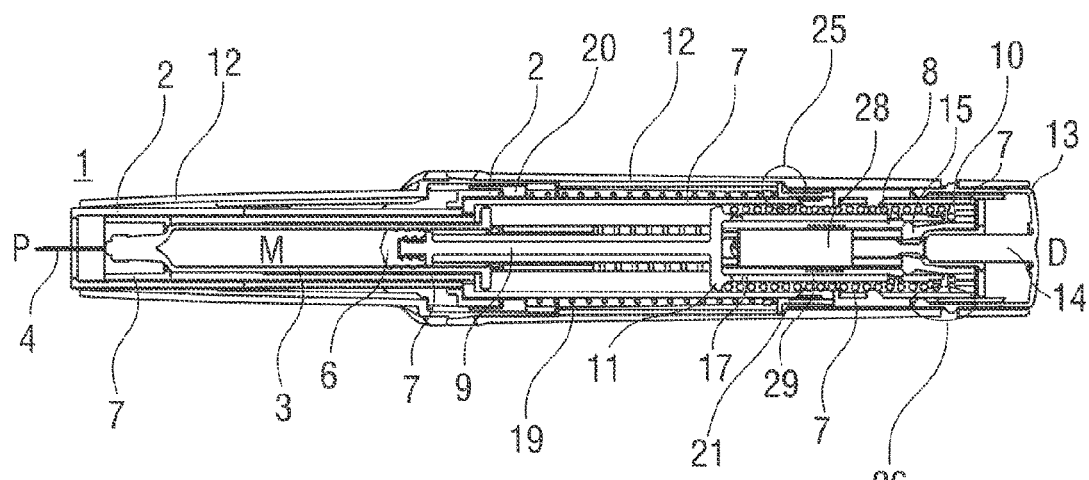

The needle 4 is now fully inserted into the injection site as illustrated in FIGS. 6A and 6B. The time between the trigger button 13 pressed and the needle 4 being fully inserted is very short, however several mechanical operations take place in this time. The needle insertion depth is defined by the carrier 7 relative to the chassis 2 not relative to the case 12, so if the user flinches or fails to hold the auto-injector 1 hard against the skin, only the case 12 will move in the distal direction D while the injection depth remains constant.

As soon as the plunger 9 has closed the gap to the stopper 6 under force of the drive spring 8 the stopper 6 is pushed in the proximal direction P within the syringe 3 displacing the medicament M through the needle 4 into the injection site.

Figure 7A:
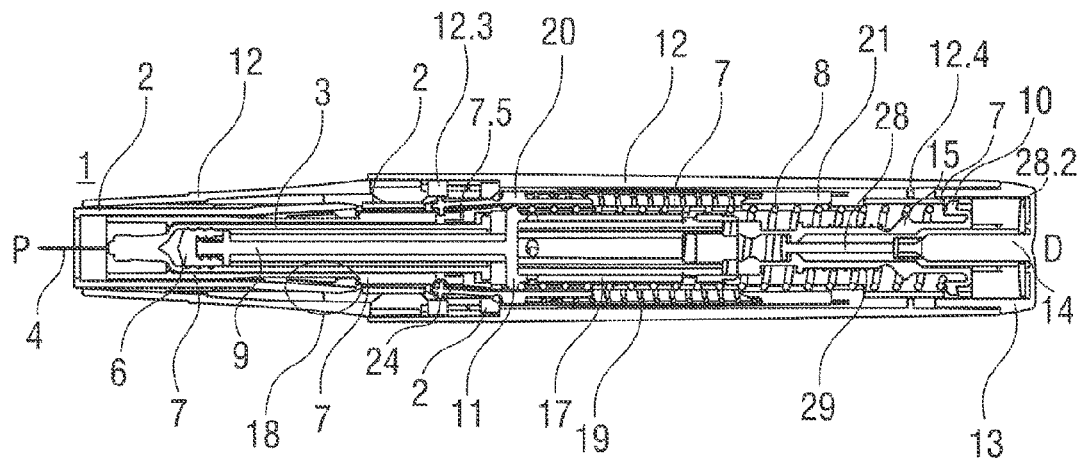
FIGS. 7A and 7B show two longitudinal sections of the auto-injector during injection near the end of dose.
Figure 7B:
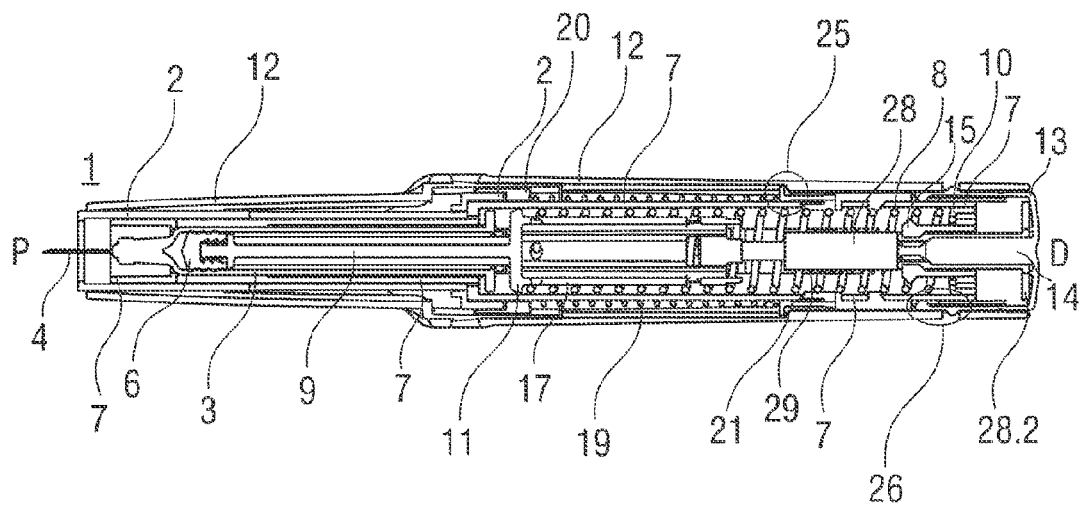

Immediately prior to the end of injection with the stopper 6 having almost bottomed out in the syringe 3 as illustrated in FIGS. 7A and 7B a noise component 28 is released. The stack up of tolerances, most notably due to the syringe 3 requires that the noise must always be released prior to the end of injection. Otherwise, with certain combinations of parts, the noise would not always release. The noise component 28 comprises an elongate portion 28.1 arranged within the distal plunger sleeve 17 and a distal end plate 28.2 arranged between the carrier end face 10 and an end face of the trigger button 13. Two second resilient arms 30 originate from the distal carrier end face 10 and extend in the proximal direction P. A noise spring 29 is arranged to bias the noise component 28 in the distal direction D relative to the carrier 7 by proximally bearing against a rib on the second resilient arms 30 and distally against the noise component 28 (not illustrated).

Figure 14A:
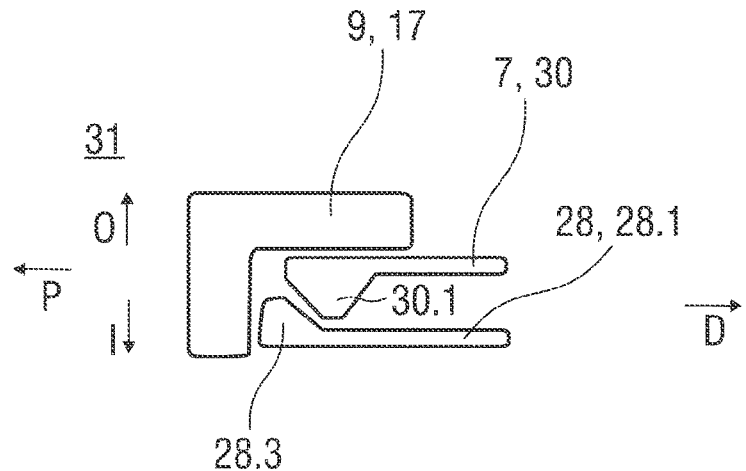
FIGS. 14A, 14B and 14C show schematic views of a noise release mechanism for audibly indicating the end of injection in three different states.
Figure 14B:
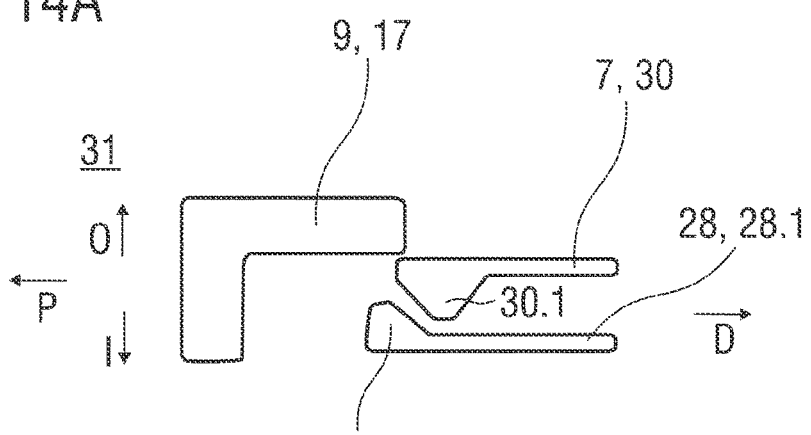
Figure 14C:
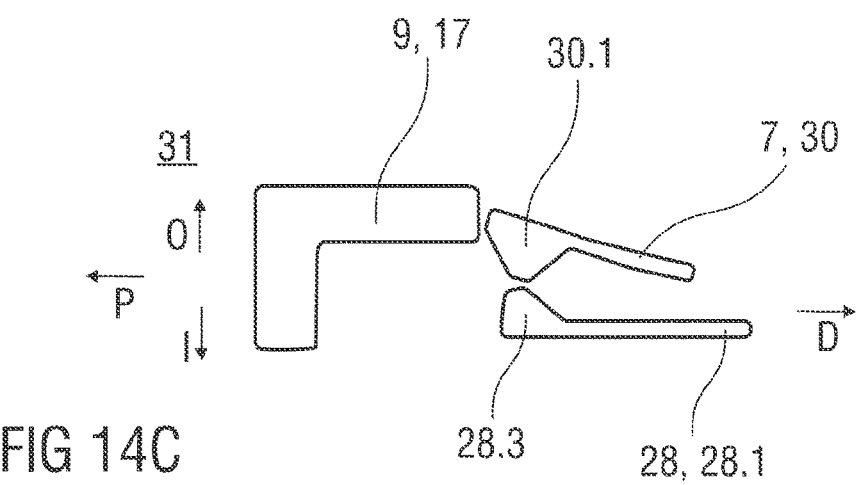

Note: the noise component 28 is not illustrated in FIGS. 16A, B and C for clarity since it does not affect the function of the button release mechanism 26. A noise release mechanism 31 for releasing the noise component 28 is schematically illustrated in FIGS. 14A, 14B and 14C. Referring now to FIG. 14A, the noise release mechanism 31 comprises the second resilient arms 30. A ramped inward boss 30.1 is arranged on each second resilient arm 30 which is engaged to a respective outward eleventh ramp 28.3 on the elongate portion 28.1 of the noise component 28 in such a manner that the second resilient arm 30 is deflected in the outward direction O under load of the noise spring 29. In an initial state A of the noise release mechanism 31 the second resilient arms 30 are prevented from being outwardly deflected by outward support of the distal plunger sleeve 17 thus preventing translation of the noise component 28 relative to the carrier 7. The noise release mechanism 31 remains in state A until immediately prior to the end of injection with the stopper 6 having almost bottomed out in the syringe 3 as illustrated in FIGS. 7A and 7B. At this point the plunger 9 has been translated in the proximal direction P relative to the carrier 7 to such an extent that the second resilient arms 30 are no longer supported by the distal plunger sleeve 17. The noise release mechanism 31 has thus arrived in a state B illustrated in FIG. 14B. Due to the ramped engagement between the ramped inward boss 30.1 and the outward eleventh ramp 28.3 the second resilient arm 30 is outwardly deflected under load of the noise spring 29 thus disengaging the noise component 28 from the carrier 7 and allowing the noise component 28 to move in the distal direction D driven by the noise spring 29 in a state C illustrated in FIG. 14C. Hence, the noise component 28 is accelerated in the distal direction D and the distal end plate 28.2 impacts on the inside of the trigger button 13 producing audible and tactile feedback to the user that the injection is about finished.

Figure 8A:
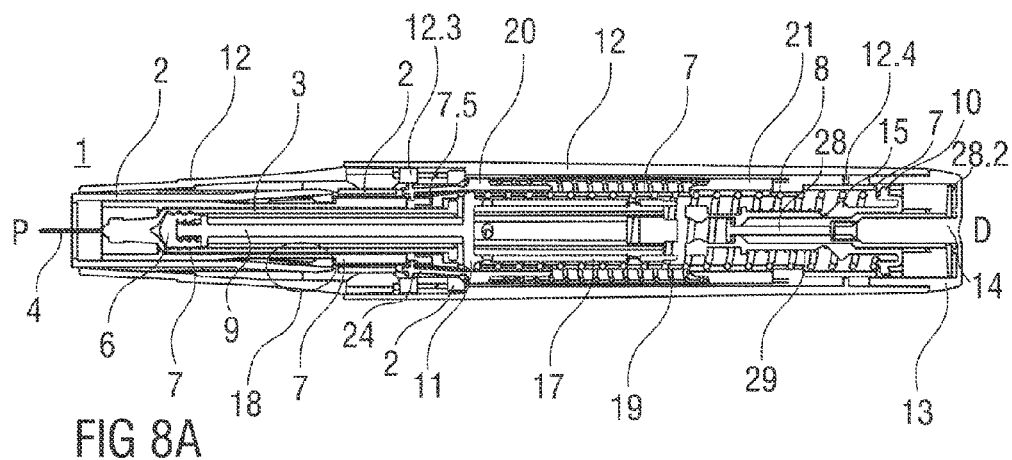
FIGS. 8A and 8B show two longitudinal sections of the auto-injector at the end of dose.
Figure 8B:
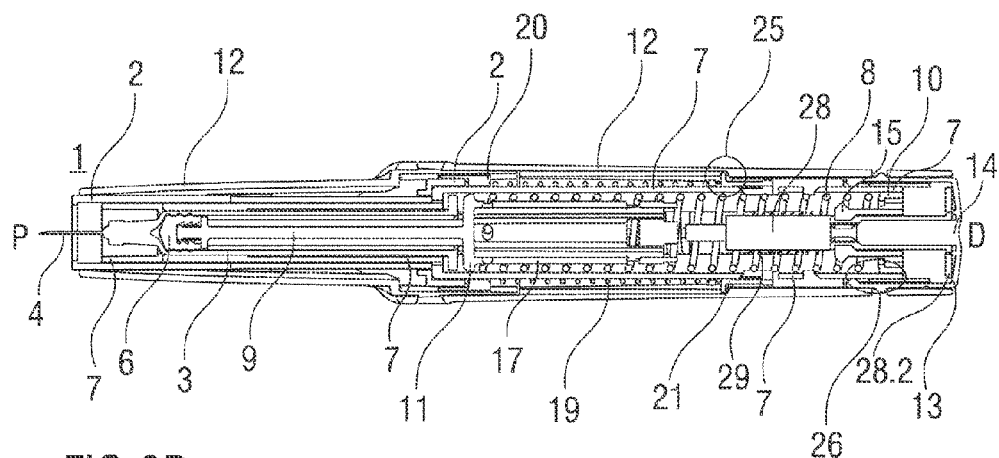

FIGS. 8A and 8B show the auto-injector 1 with the stopper 6 having entirely bottomed out in the syringe 3.

Figure 9A:
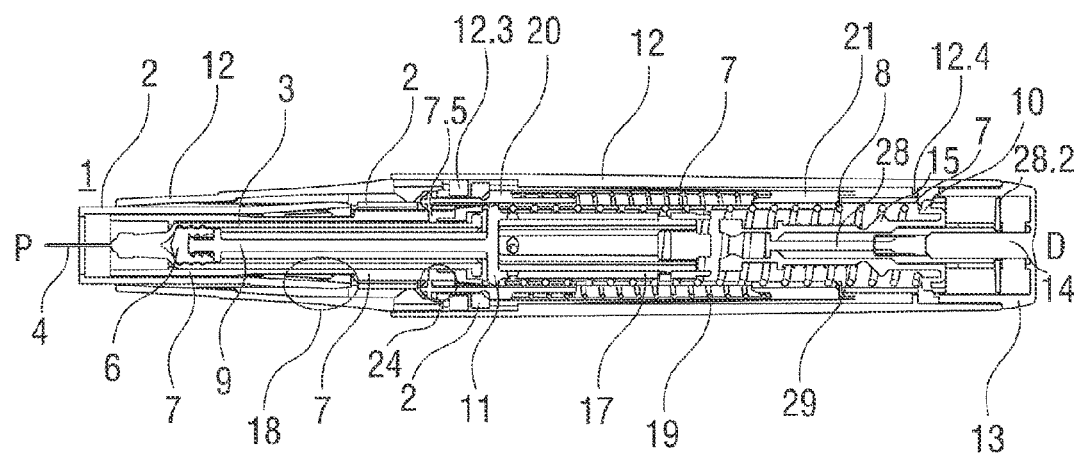
FIGS. 9A and 9B show two longitudinal sections of the auto-injector removed from the injection site.
Figure 9B:
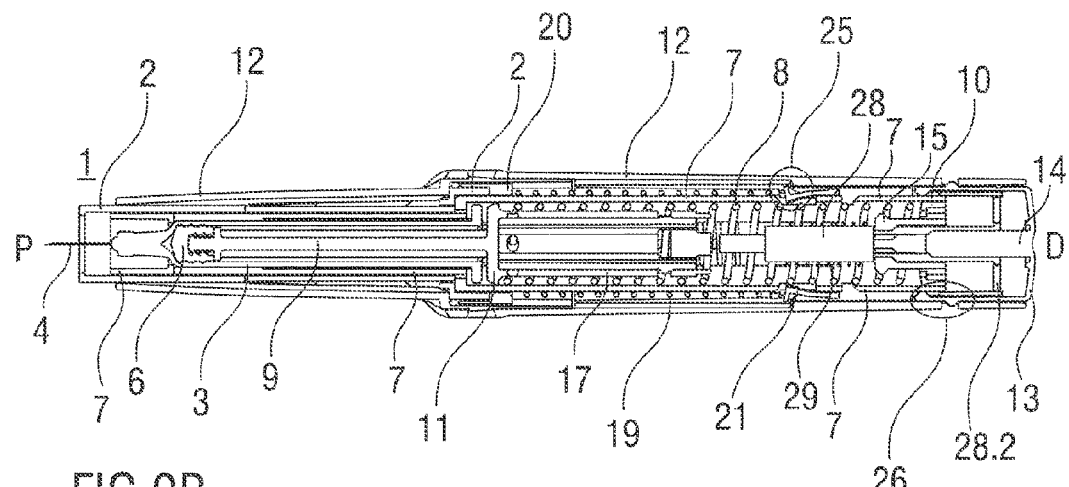

As mentioned above the user is able to let the case 12 move by a few millimeters in the distal direction D under the force of the control spring 19 without affecting the position of the needle 4 as long as that motion is below a predefined distance. If the user wishes to end the injection, at any time, they must allow the case 12 to move in the distal direction D beyond that distance. FIGS. 9A and 9B show the auto-injector 1 lifted from the injection site with the case 12 moved all the way in the distal direction D so that the chassis 2 protrudes from the proximal end of the case 12. As the case 12 is moved the first collar 20 releases the carrier 7 and then the second collar 21 releases from the case 12 and pulls the carrier 7 in the distal direction D. The sequencing of this switching is critical as retraction will fail if both collars 20, 21 are attached to the carrier 7 at the same time. This is overcome by separating the switching of the collars 20, 21 by a significant displacement of the case 12.

Figure 12E:
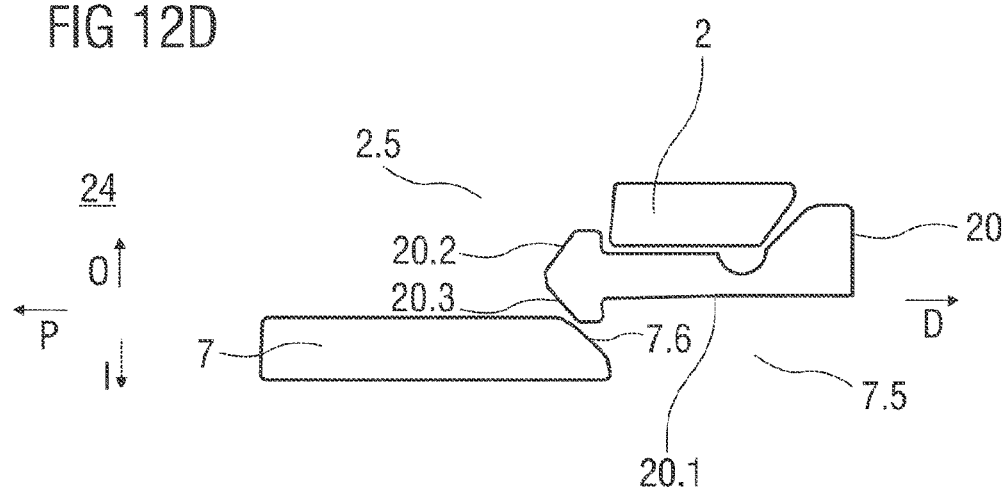
Figure 12F:
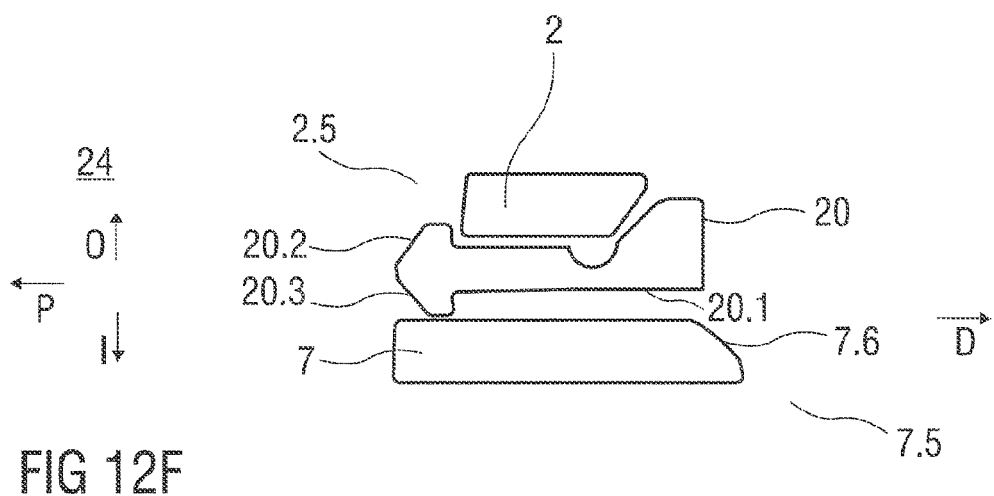

The switching of the first collar 20 is illustrated in FIGS. 12E and F. In FIG. 12E the case 12 has been allowed to move in the distal direction D under load of the control spring 19 during removal of the auto-injector 1 from the injection site. The first rib 12.3 (not illustrated, see FIG. 9A) is removed from outwardly behind the arrowhead 20.1. The first collar 20 is still being pushed in the proximal direction P by the control spring 19. Due to the engagement of the inward ninth ramp 20.3 on the arrowhead 20.1 with the distal tenth ramp 7.6 on the carrier 7 the arrowhead 20.1 is deflected in the outward direction O into the aperture 2.5 of the chassis 2 (illustrated in FIGS. 12A to 12F), the needle insertion control mechanism 24 arriving in a state E as illustrated in FIG. 12E, decoupling the first collar 20 from the carrier 7 and latching it to the chassis 2.

Figure 13B:
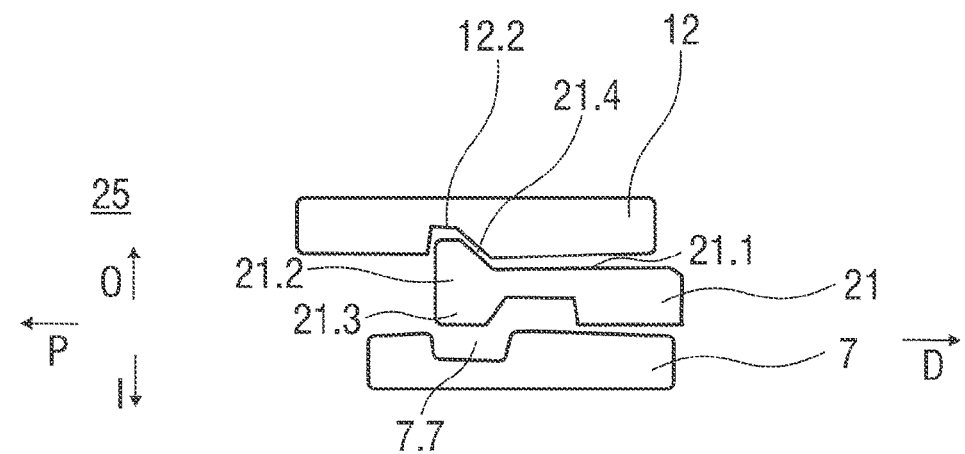
Figure 13C:
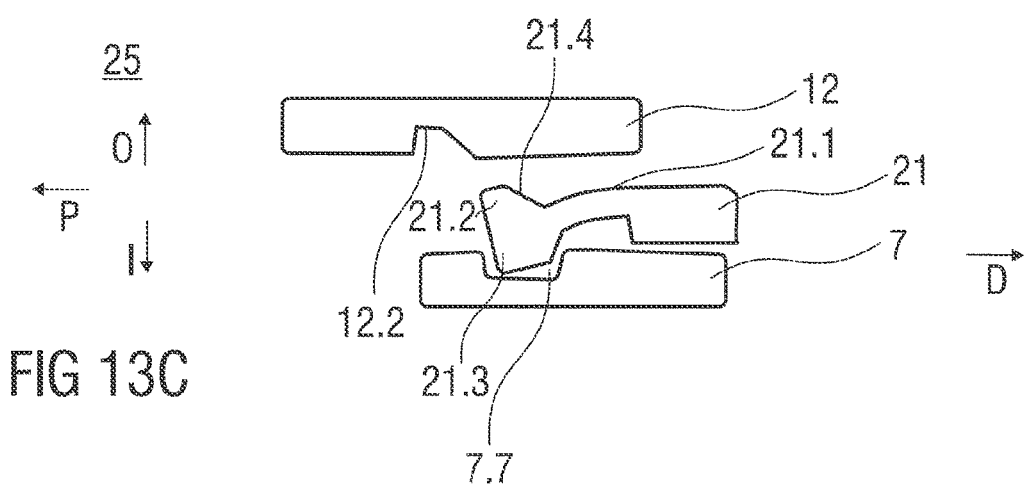

As the case 12 is moving further in the distal direction D on removal from the injection site the syringe retraction control mechanism 25 switches from its state A (cf. FIG. 13A) into a state B illustrated in FIG. 13B. The case 12 and the second collar 21 locked to the case 12 move together in the distal direction D while the carrier 7 is held in place by the detent mechanism 18 in its state C as described above (cf. FIG. 11C). Due to this motion the inward boss 21.3 on the second beam head 21.2 of the proximal beam 21.1 on the second collar 21 no longer inwardly abuts the carrier 7. Instead the inward boss 21.3 is deflected in the inward direction I into a third recess 7.7 in the carrier 7 due to the ramped engagement of the second beam head 21.1 to the ramped second case detent 12.2 under load of the control spring 19. The syringe retraction control mechanism 25 thus arrives in a state C as illustrated in FIG. 13C with the second collar 21 decoupled from the case 12 and coupled to the carrier 7. The detent mechanism 18 applies a small retarding force to the movement of the carrier 7 before the syringe retraction control mechanism 25 switches to state C as there is a small sliding force, applied by the second collar 21, pulling the carrier 7 in the distal direction D on translation of the case 12 in the distal direction D when the needle insertion control mechanism 24 has already been switched into state E. If the carrier 7 moves too far in the distal direction D before the second collar 21 switches, the case 12 runs out of travel before the inward boss 21.3 can deflect into the third recess 7.7 preventing retraction.

Starting from the position C of the detent mechanism 18 (cf. FIG. 11C) the carrier 7 and hence the rhomboid ramp member 7.1 are translated in the distal direction D under load of the control spring 19. Hence, the distal fifth ramp 7.3 of the rhomboid ramp member 7.1 engages the proximal third ramp 2.3 on the first beam head 2.2 of the resilient beam 2.1 in a manner deflecting the resilient beam 2.1 in the inward direction I. This applies the small retarding force to the movement of the carrier 7 required for ensuring the switching of the second collar 21 to the carrier 7. The resilient beam 2.1 and the rhomboid ramp member 7.1 are offset sideways to allow the resilient beam 2.1 to pass without contacting the rhomboid ramp member 7.1 as soon as the first beam head 2.2 is entirely inwardly from the ramp member 7.1 in a state D illustrated in FIG. 11D.

Figure 11D:
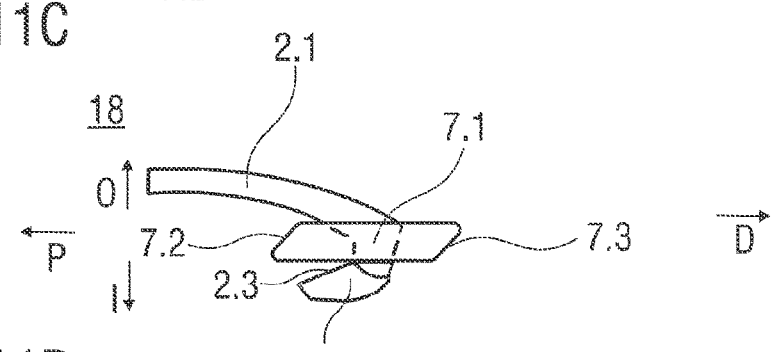

The control spring 19 is grounded at its proximal end in the case by the first collar 20 being abutted against the chassis 2. The distal end of the control spring 19 moves the second collar 21 in the distal direction D taking with it the carrier 7 and hence the syringe 3 with the needle 4 overcoming the detent mechanism 18 as illustrated in FIG. 11D. Note that the needle 4 is retracted out of the skin by the auto-injector 1 as soon as the user allows the case 12 to translate sufficiently far as opposed to auto-injectors with needle shields which require the user to remove the auto-injector from the injection site thereby themselves pulling the needle out of the skin for allowing the needle shield to advance.

As the movement allowed of the noise component 28 is limited relative to the carrier 7 it is no longer in contact with the trigger button 13 which has moved in the distal direction D with the case 12 on removal from the injection site. When the retraction begins the noise spring 29 does not provide any retarding force. Once the noise component 28 hits the trigger button 13 again on retraction of the carrier 7 the noise spring 29 must be recompressed, reducing the force driving the final part of retraction. In order to ensure a reliable retraction despite this reducing force the control spring 19 must be appropriately dimensioned.

Figure 10A:
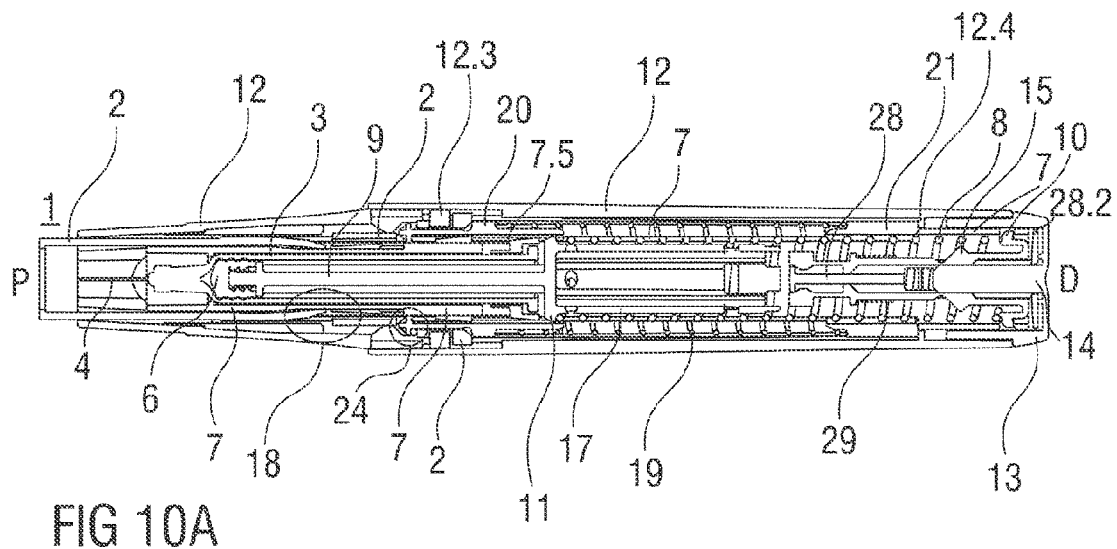
FIGS. 10A and 10B show two longitudinal sections of the auto-injector with the needle retracted into a needle safe position.
Figure 10B:
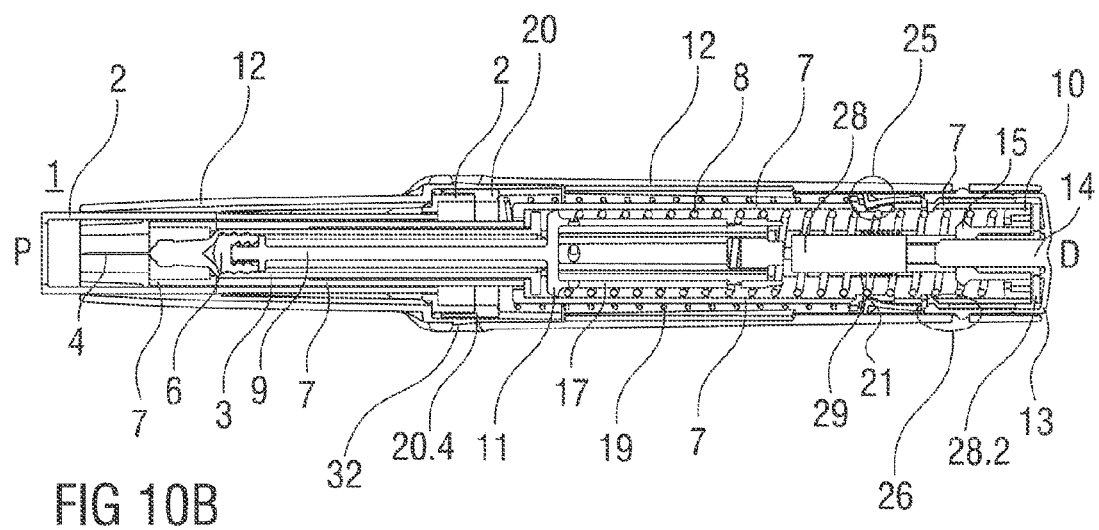

The retraction ends when the distal collar 21 meets a first back stop 12.4 on the case 12 as in FIGS. 10A and 10B. The arrowhead 20.1 on the first collar 20 is inwardly supported by the carrier 7 in a state F illustrated in FIG. 12F and thus prevented from deflecting in the inward direction I. The outward sixth ramp 20.2 of the arrowhead 20.1 is engaged behind the first rib 12.3 on the case 12 preventing the case 12 from being pushed in the proximal direction P again. A clearance may be provided between the arrowhead 20.1 and the first rib 12.3 to allow for tolerances.

The detent mechanism 18 returns to state A as in FIG. 11A locking the carrier 7 in position relative to the chassis 2 as it did initially, however it cannot be unlocked now as the case 12 cannot move relative to the chassis 2.

A tab 20.4 on the first collar 20 is now visible through an indicator window 32 in the case 12—indicating the auto-injector 1 has been used.

Figure 17:
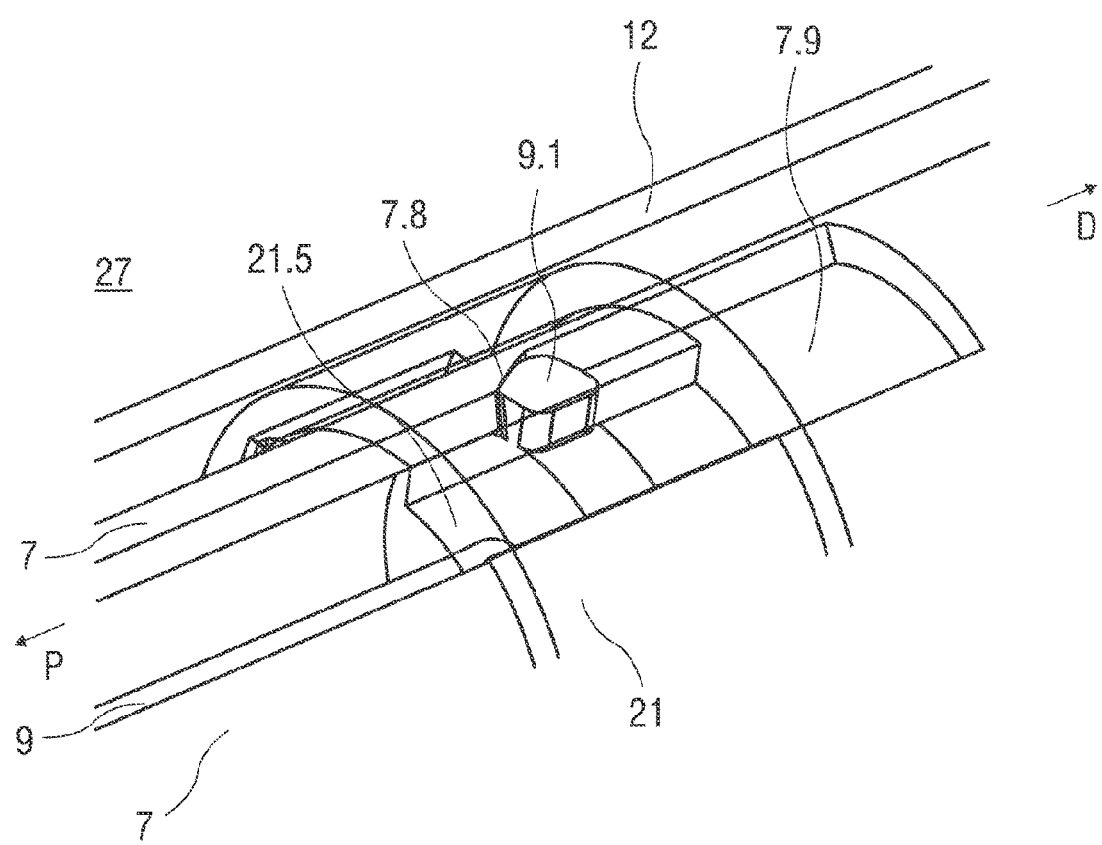
FIG. 17 is an isometric view of an alternative embodiment of the plunger release mechanism.

FIG. 17 is an isometric view of an alternative embodiment of the plunger release mechanism 27. The plunger release mechanism 27 prevents movement of the plunger 9 in the proximal direction P relative to the carrier 7 until the carrier 7 is moved in the proximal direction P for needle insertion. As opposed to the plunger release mechanism 27 of FIG. 15, where relative movement of the carrier 7 and trigger button 13 are used to trigger the release of the plunger 9, the alternative embodiment of FIG. 17 releases the plunger 9 by movement of the carrier 7 relative to the second collar 21. FIG. 17 illustrates the plunger release mechanism 27 prior to plunger release. The second collar 21 is shown transparent to improve clarity. The plunger 9 is being pushed in the proximal direction P by the drive spring 8. In order for the plunger 9 to advance, it must rotate around a twelfth ramp 7.8 on the carrier 7. A ramp member 9.1 on the plunger 9 is arranged to engage this twelfth ramp 7.8. Rotation of the ramp member 9.1 is blocked by an inward longitudinal rib 21.5 on the second collar 21 splined in a longitudinal aperture 7.9 in the carrier 7. The case 12 and the second collar 21 remain in the same position, i.e. coupled to each other for joint axial translation. On depression of the trigger button 13 the carrier 13 and the plunger 9 being part of the drive sub-assembly are moved in the proximal direction P, first by the user pressing the trigger button 13 and then by the control spring 19 taking over via the first collar 20 as described above. Once the carrier 7 moves sufficiently far in the proximal direction P relative to the second collar 21 the ramp member 9.1 on the collar 9 comes clear of the longitudinal rib 21.5 on the second collar 21 and can rotate past the proximal end of the longitudinal rib 21.5 due to its ramped engagement to the twelfth ramp 7.8 under load of the drive spring 8. Hence, the drive spring 8 advances the plunger 9 in the proximal direction P for injecting the medicament M.

Figure 18:
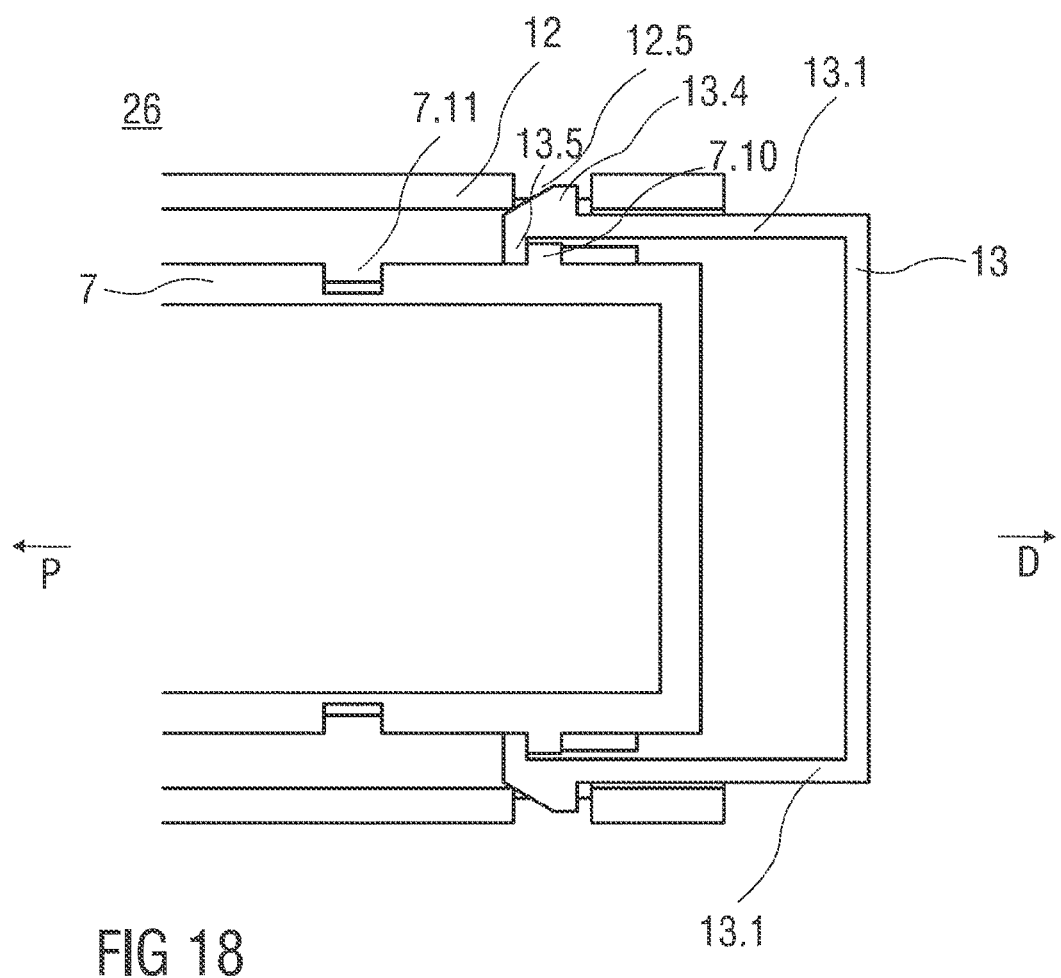
FIG. 18 is a longitudinal section of an alternative embodiment of the button release mechanism.

FIG. 18 is a longitudinal section of an alternative embodiment of the button release mechanism 26. Other than the button release mechanism 26 of FIG. 16 which gives the appearance of a revealing trigger button 13 on skin contact by switching the ground of the trigger button 13 between the carrier 7 and the case 12, the button release mechanism 26 of FIG. 18 starts with the trigger button 13 locked but protruding from the distal end of the case 12. Once the carrier 7 has moved in the distal direction D on skin contact of the chassis 2, it is possible to depress the trigger button 13 and activate the auto-injector 1. This ensures a sequenced operation.

In the embodiment of FIG. 18 the trigger button 13 has two proximal beams 13.1, each of them having a ramped outward boss 13.4. In the initial state shown in FIG. 18 the ramped outward bosses 13.4 are engaged in respective fourth recesses 12.5 in the case 12. Disengaging the ramped outward bosses 13.4 from the fourth recesses 12.5 is prevented by the carrier 7 inwardly supporting the proximal beams 13.1 in a manner to keep the proximal beams 13.1 from deflecting inwardly. Inward protrusions 13.5 on the proximal beams 13.1 abut against a second rib 7.10 on the carrier 7 in a manner preventing the carrier 7 from moving further in the proximal direction P in the initial state. Once the carrier 7 has moved in the distal direction D on skin contact of the chassis 2 a first window 7.11 in the carrier 7 is moved behind the inward protrusion 13.5 so as to allow the proximal beams 13.1 to be inwardly deflected due to their ramped engagement in the fourth recesses 12.5 on depression of the trigger button 13. The proximal beams 13.1 are now outwardly supported by the case 12 and remain engaged to the carrier 7 even on retraction of the needle 4. The trigger button 13 does therefore not return to its initial position, indicating that the auto-injector 1 has been used.

The button release mechanism 26 illustrated in FIG. 18 may preferably be combined with the plunger release mechanism 27 illustrated in FIG. 17.

Figure 19A:
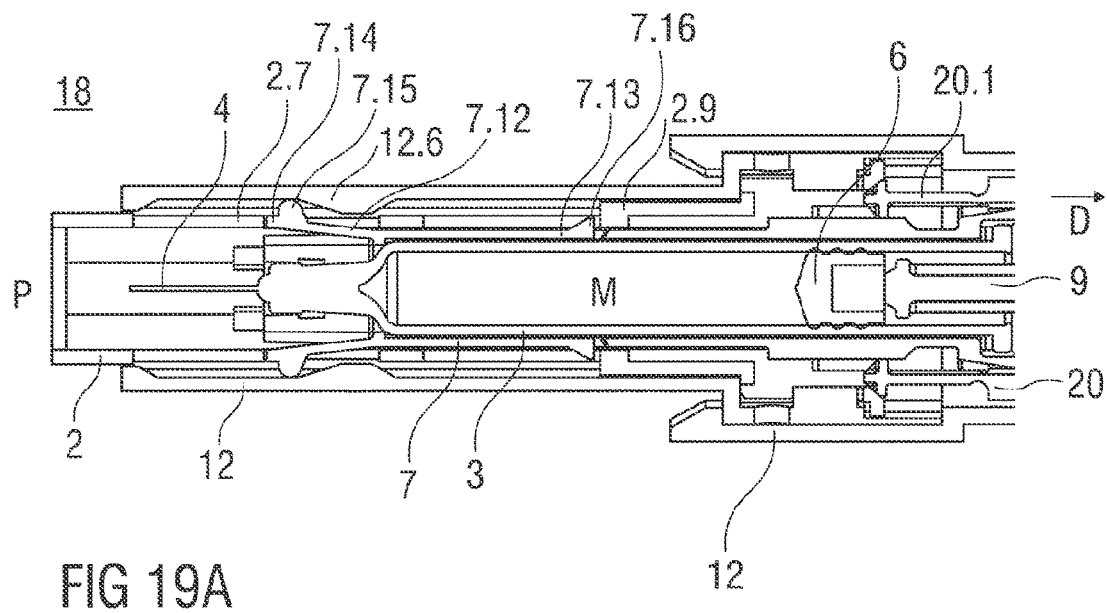
FIGS. 19A and 19B show longitudinal sections of an alternative embodiment of the detent mechanism.
Figure 19B:
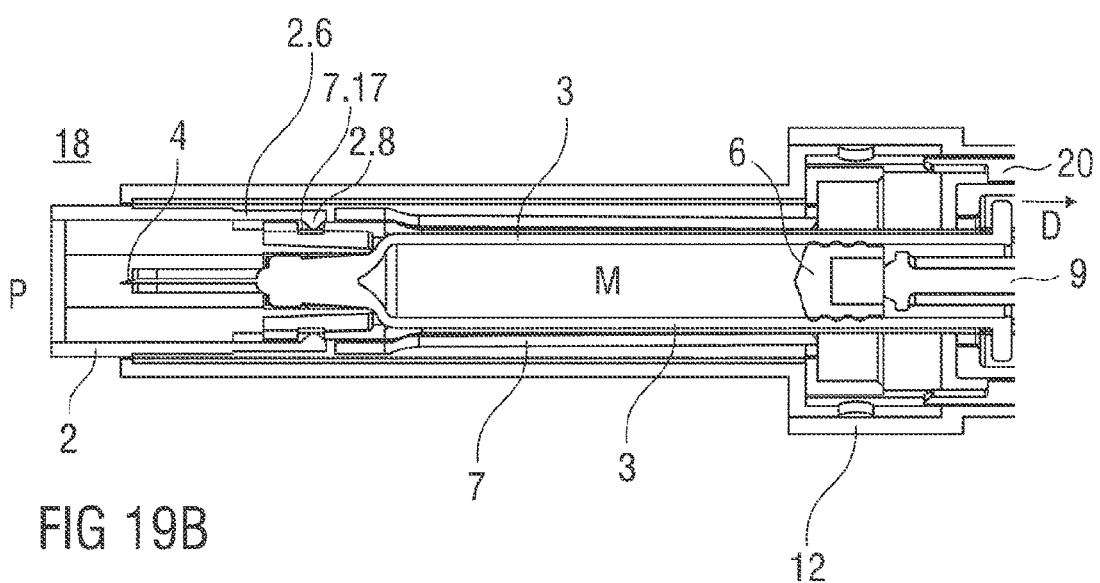

FIGS. 19A and 19B show two longitudinal sections of an alternative embodiment of the detent mechanism 18. The detent mechanism 18 of FIGS. 11A to 11D, which may be referred to as a "race track" mechanism because of the first beam head 2.2 travelling around the rhomboid ramp member 7.1 has multiple functions which control the movement of the carrier 7 relative to the chassis 2. The alternative detent mechanism 18 of FIGS. 19A and 19B uses three clips 7.12, 7.13, 2.6 to produce the same effect.

The first clip 7.12 is arranged as an outwardly biased resilient beam on the carrier 7 extending from the carrier 7 in the proximal direction P. the first clip 7.12 is arranged to prevent the carrier 7 from being moved in the proximal direction P prior to the chassis 2 being depressed or rather the case 12 being translated on skin contact. The first clip 7.12 is composed of two sections side by side. A first section 7.14 prevents movement of the carrier 7 in the proximal direction P by abutting the chassis 2 in a recess. A second section 7.15 is arranged as an outwardly protruding clip head arranged to be ramped inwards by a ramp feature 12.6 on the chassis 12 for releasing the first clip 7.12 thereby unlocking the carrier 7 from the chassis 2 when the case 12 is being translated in the proximal direction P on skin contact. A longitudinal slot 2.7 in the chassis 2 is arranged for allowing the second section 7.15 to slide in the proximal direction P once the lock has been released. A slight friction force between the first clip 7.12 and the chassis 2 provides the retarding force required to ensure retraction.

The second clip 7.13 is arranged as a resilient beam on the carrier 7 extending in the distal direction D having an outwardly protruding third beam head 7.16 with a proximal ramp. The third beam head 7.16 serves as a back stop against a third rib 2.9 on the chassis 2 for preventing the carrier 7 moving in the distal direction D from its initial position. The carrier 7 and chassis 2 are assembled with the second clip 7.13 in this position prior to inserting the syringe 3 into the carrier 7 which is facilitated by the proximal ramp on the third beam head 7.16. The syringe 3 locks the clip in place by preventing inward deflection thus creating a fixed stop.

The third clip 2.6 is a resilient beam on the chassis 2 extending in the distal direction D. A ramped fourth beam head 2.8 on the third clip 2.6 is arranged to inwardly engage in a fifth recess 7.17 in the carrier 7. Once the first clip 7.12 is unlocked, the user can load the third clip 2.6 by pressing the carrier 7 in the proximal direction P on depression of the trigger button 13. The third clip 2.6 is loaded in compression, i.e. it will bend outwards and release suddenly due to its ramped engagement to the carrier 7 providing the detent functionality similar to that illustrated in FIG. 11B.

Figure 20:
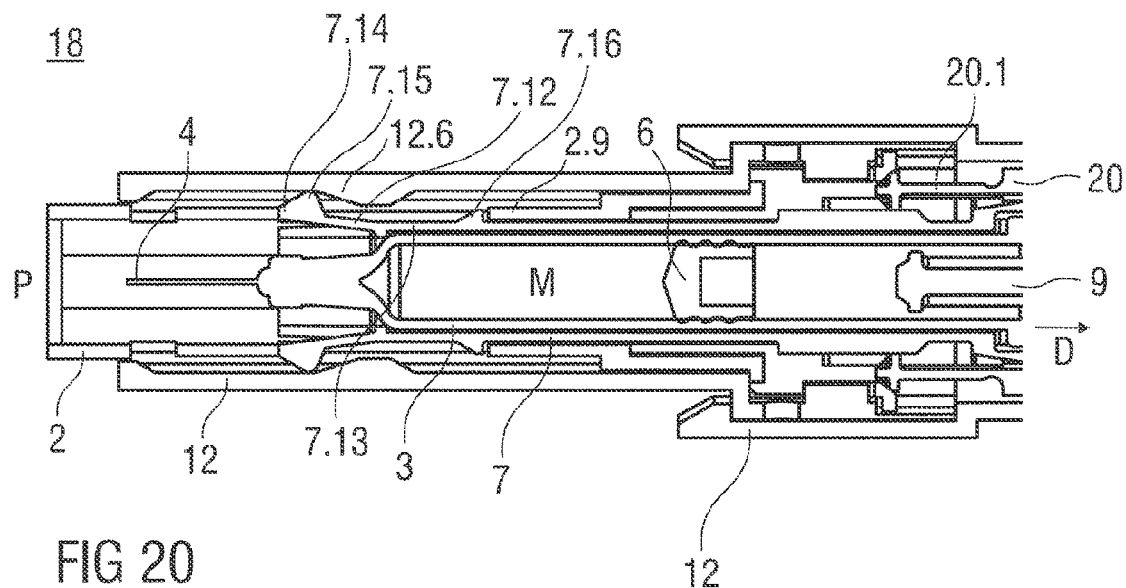
FIG. 20 is a longitudinal section of a third embodiment of the detent mechanism.

FIG. 20 is a longitudinal section of a third embodiment of the detent mechanism 18 which is a variation on the embodiment of FIGS. 19A and 19B. In this embodiment the detent function of the third clip 2.6 has been added into the first clip 7.12. The lock between the case 12 and the carrier 7 is released in the same way, but the detent is provided by deflecting the first clip 7.12 inwards a second level which is achieved by the chassis 2 not having a slot 2.7 for the second section 7.15. Instead the second section 7.15, once ramped inwards by the ramp feature 12.6 on the case 12 has to be further ramped inwards inside the chassis 2 on axial load between the chassis 2 and the carrier 7, suddenly releasing their engagement.

Figure 21:
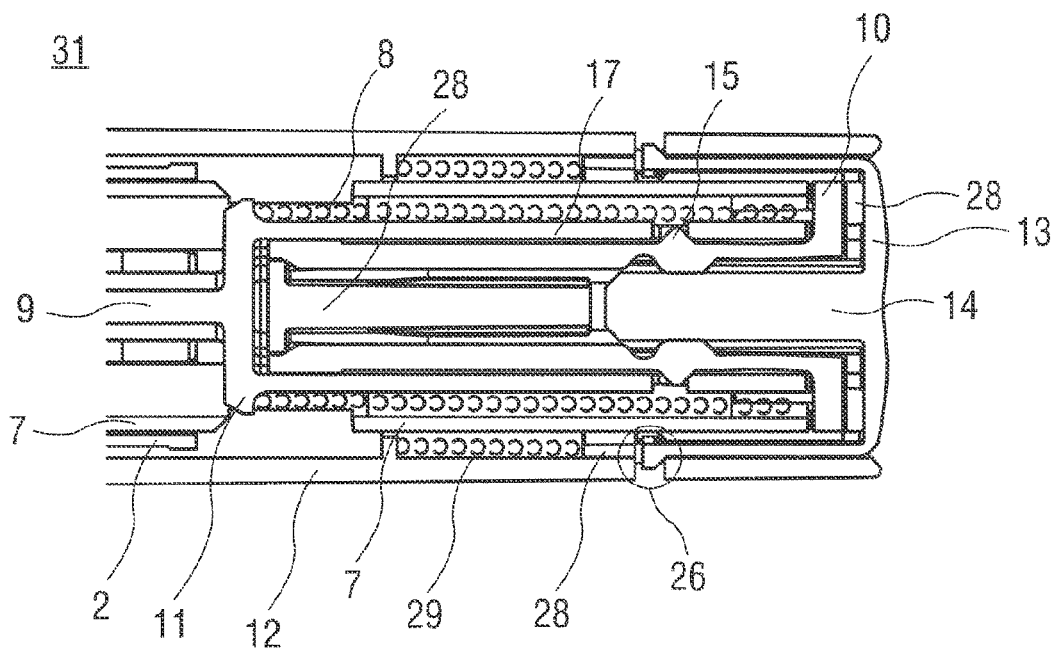
FIG. 21 is a longitudinal section of an alternative embodiment of the noise release mechanism.

FIG. 21 is a longitudinal section of an alternative embodiment of the noise release mechanism 31. As opposed to the noise release mechanism 31 of FIG. 14 where the noise spring 29 acts between the carrier 7 and the noise component 28, in the embodiment illustrated in FIG. 21 the noise spring 29 acts between the case 12 and the noise component 28. During needle insertion the noise spring 29 is compressed as the noise component 28 moves with the carrier 7 relative to the case 12. When the noise component 28 is released by the plunger 9 shortly before the end of dose, the noise component 28 moves in the distal direction D and impacts the trigger button 13. Other than in FIG. 14 the noise spring 29 is not being recompressed during needle retraction since it is grounded in the case 12 not in the carrier 7.

Figure 22A:
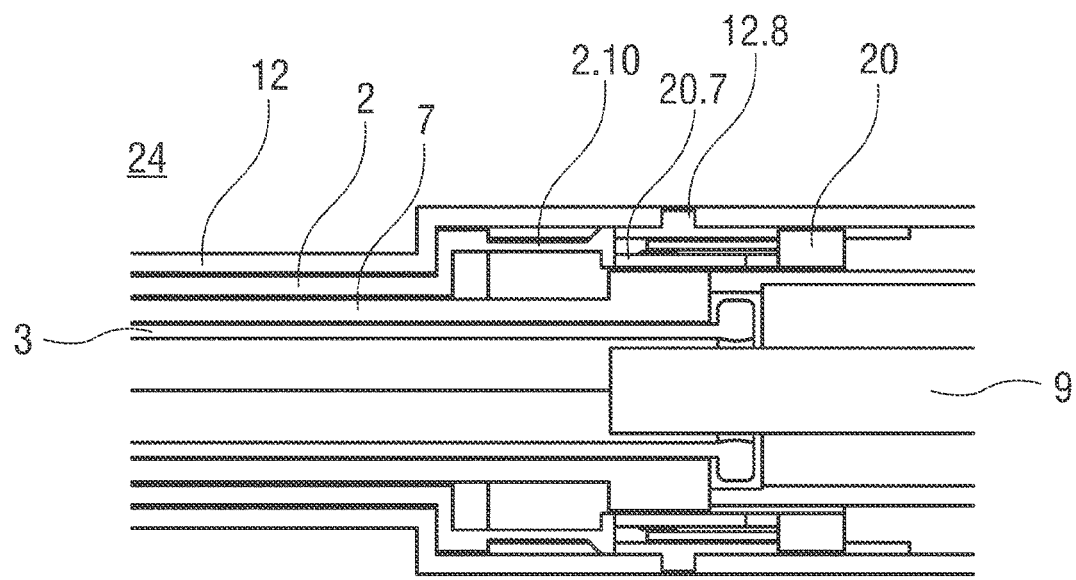
FIGS. 22A and 22B show longitudinal sections of an alternative embodiment of the needle insertion control mechanism, also arranged to perform the function of the detent mechanism on needle retraction and needle insertion.
Figure 22B:
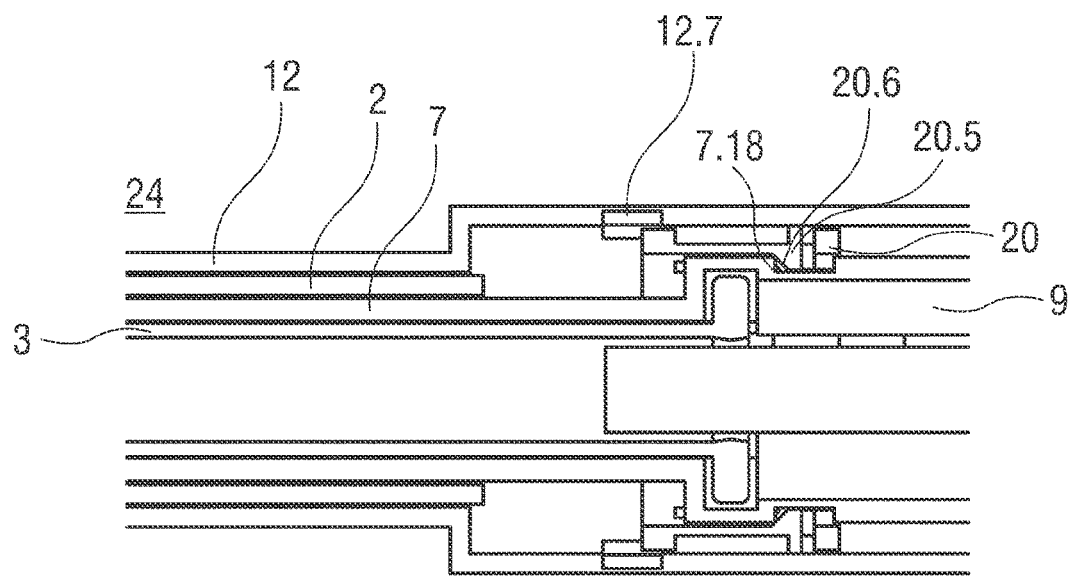
Figure 23:
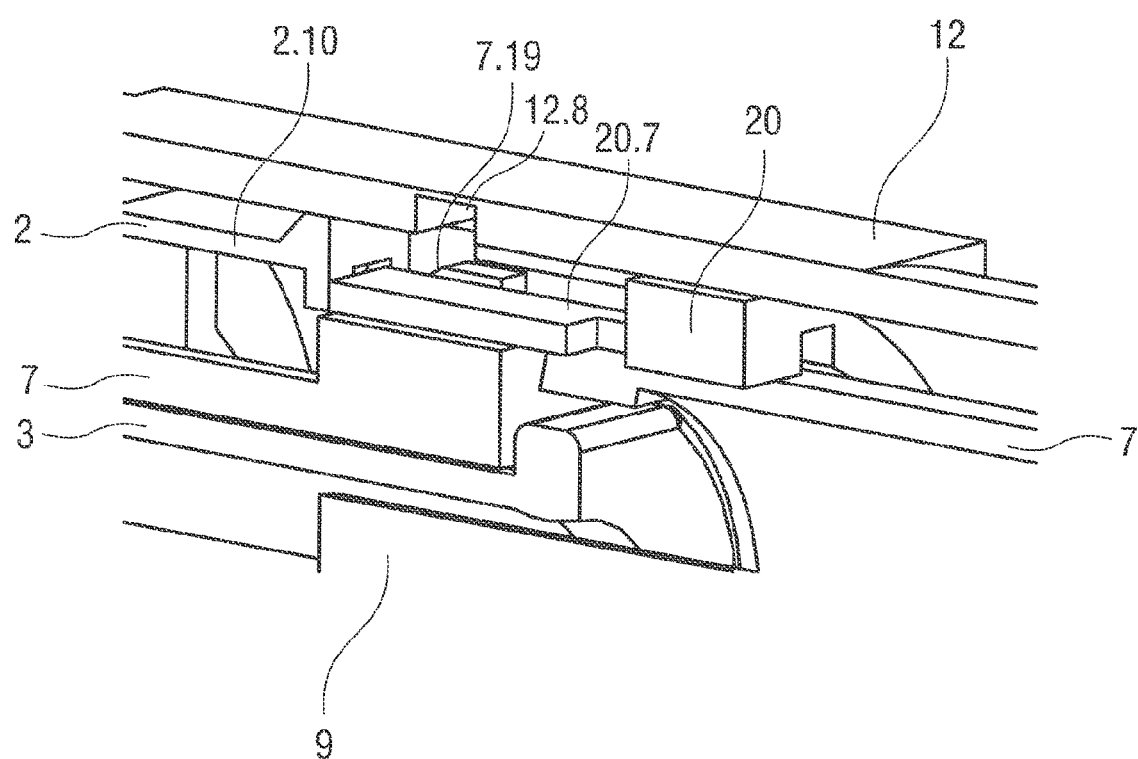
FIG. 23 is an isometric view of the needle insertion control mechanism of FIG. 22, FIGS. 24A and 24B show longitudinal sections of a third embodiment of the needle insertion control mechanism, also arranged to perform the functions of the detent mechanism.

FIGS. 22A and 22B show longitudinal sections of an alternative embodiment of the needle insertion control mechanism 24 which is also arranged to perform the detent function of the detent mechanism 18 on needle retraction and needle insertion. FIG. 23 shows a corresponding isometric view. A fourth clip 20.5 on the first collar 20 is arranged as a resilient beam with a beam head having an inward proximal thirteenth ramp 20.6 for engaging a fourth rib 7.18 on the carrier 7 and outwardly supported by the case 12 so as to keep the first collar 20 engaged to the carrier 7 prior to use, during needle insertion and during injection. When the user lifts the case 12 away from the injection site at the end of injection, a sixth recess 12.7 in the case 12 is moved outwardly behind the fourth clip 20.5 allowing the fourth clip 20.5 to release when the carrier 7 is pulled in the distal direction D by the second collar 21. Since the fourth clip 20.5 has to be ramped outwards a small force is required to release the fourth clip 20.5, providing the retraction detent.

A fifth clip 2.10 on the chassis 2 abuts a block 20.7 on the first collar 20 prior to use preventing the first collar 20 and hence the carrier 7 engaged to the first collar 20 from moving in the proximal direction P. In order to release, the fifth clip 2.10 must be deflected outwards and over the block 20.7. Outward deflection of the fifth clip 2.10 is initially prevented by the case 12. Once the case 12 has moved on skin contact a second window 12.8 in the case 12 appears outwardly from the fifth clip 2.10 allowing outward deflection. The fifth clip 2.10 is then deflected by a fourteenth ramp 7.19 on the carrier 7 when the carrier 7 is pushed in the proximal direction P on button depression as the fourth clip 20.5 does allow translation of the carrier 7 in the proximal direction P relative to the first collar 20 but not the other way round. The detent for needle insertion is provided by having to deflect the fifth clip 2.10 when it is loaded by the control spring 19.

Figure 24A:
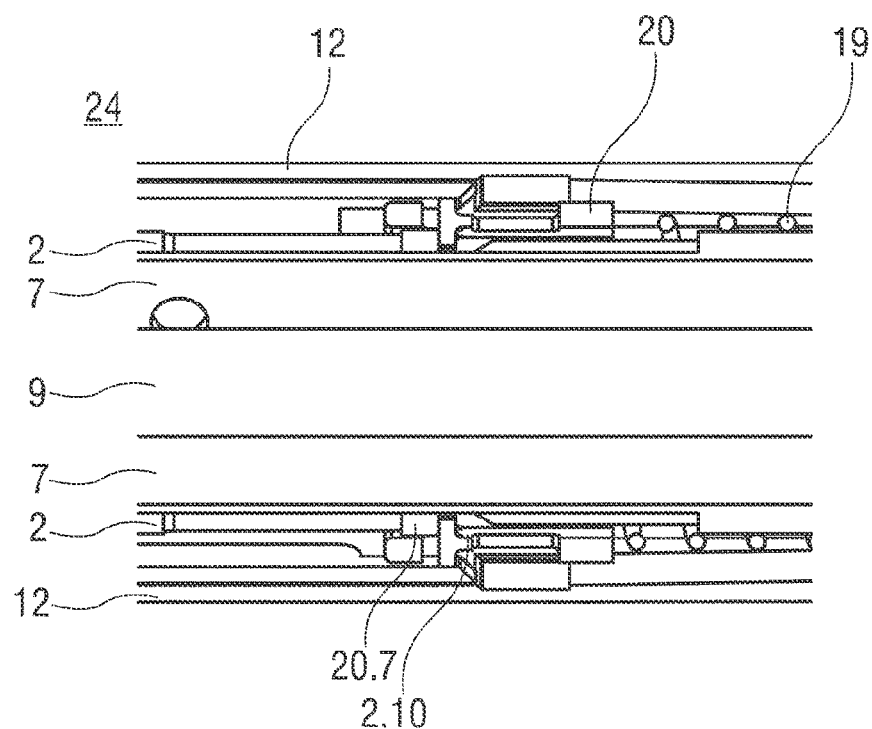
Figure 24B:
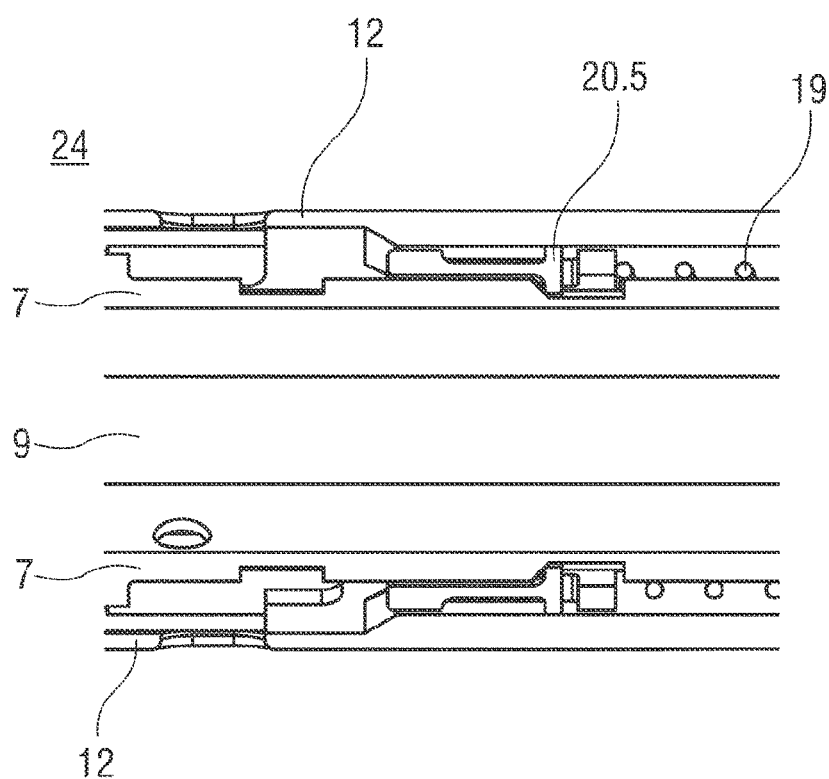
Figure 25:
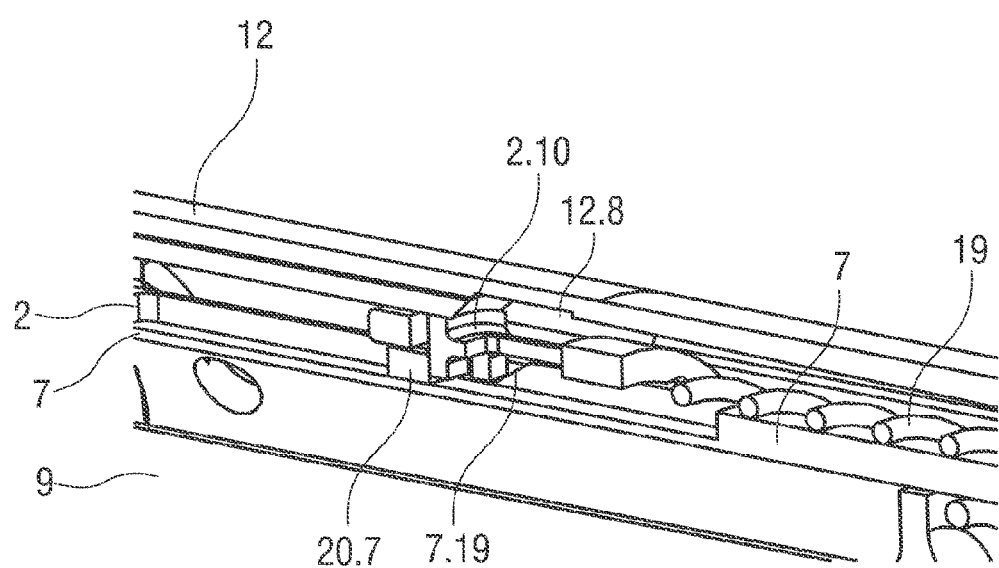
FIG. 25 is an isometric view of the needle insertion control mechanism of FIG. 24, FIGS. 26A and 26B show longitudinal sections of a third embodiment of the noise release mechanism.

FIGS. 24A and 24B show longitudinal sections of a third embodiment of the needle insertion control mechanism 24, also arranged to perform the functions of the detent mechanism 18. FIG. 25 is an isometric view of the needle insertion control mechanism 24 of FIG. 24. The embodiment is similar to that illustrated in FIGS. 22A, 22B and 23. The difference is that the fifth clip 2.10 is arranged on the first collar 20 and the block 20.7 is arranged on the chassis 2, i.e. their position has been switched, so there are two clips 2.10 and 20.5 on the first collar 20.

The fourth clip 20.5 is identical to that in FIG. 22B. It keeps the first collar 20 connected to the carrier 7 until the needle retraction is triggered, ensuring full injection depth is reached and maintained until the retraction cycle is initiated by removing the auto-injector 1 from the skin.

The fifth clip 2.10 provides the detent for needle insertion and releases the first collar 20 from the chassis 2, initiating needle insertion. The fifth clip 2.10 prevents the first collar 20 and hence the carrier 7 engaged to the first collar 20 from moving in the proximal direction P prior to use by abutting the block 20.7 on the chassis 2. In order to release, the fifth clip 2.10 must be deflected outwards and over the block 20.7. Outward deflection of the fifth clip 2.10 is initially prevented by the case 12. Once the case 12 has moved on skin contact the second window 12.8 in the case 12 appears outwardly from the fifth clip 2.10 allowing outward deflection. The fifth clip 2.10 is then deflected by the fourteenth ramp 7.19 on the carrier 7 when the carrier 7 is pushed in the proximal direction P on button depression as the fourth clip 20.5 does allow translation of the carrier 7 in the proximal direction P relative to the first collar 20 but not the other way round. The detent for needle insertion is provided by having to deflect the fifth clip 2.10 when it is loaded by the control spring 19.

Figure 26A:
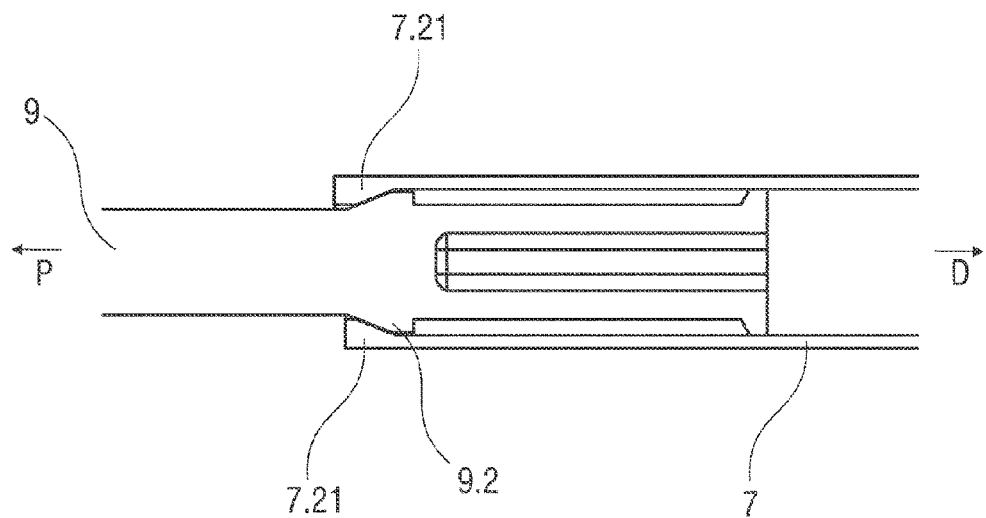
Figure 26B:
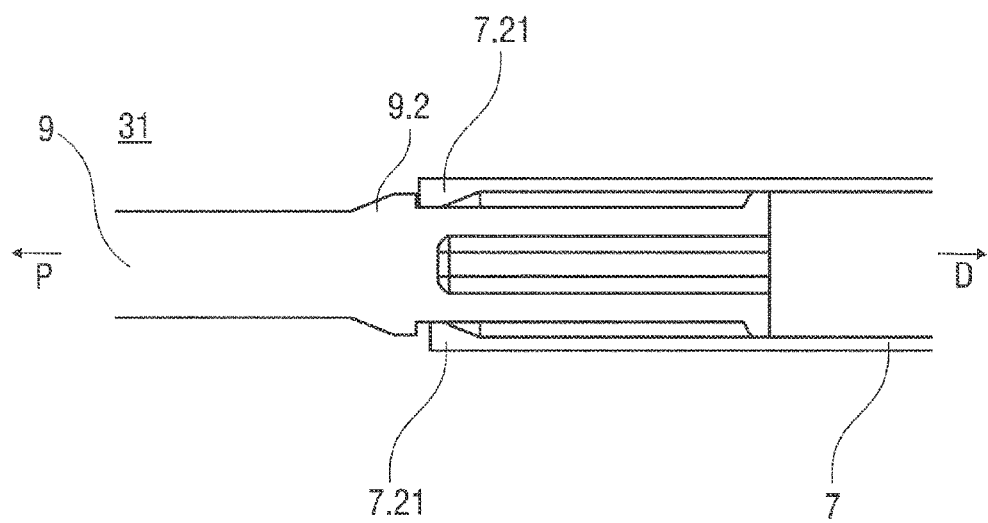

FIGS. 26A and 26B show a longitudinal section of a third embodiment of the noise release mechanism 31. This embodiment works without the need for a dedicated noise spring. The plunger 9 comprises a proximally ramped rib 9.2 arranged to splay two seventh clips 7.21 on the carrier 7 immediately prior to the end of dose. When the proximally ramped rib 9.2 has travelled past the seventh clips 7.21 they snap back and impact the plunger 9 generating a sound. The tubular shape of the carrier 7 helps to transmit the sound. FIG. 26A shows the noise release mechanism 31 before release. FIG. 26B shows the noise release mechanism 31 after release. Proximal faces of the seventh clips 7.21 on the carrier 7 are axially offset to facilitate assembly by lifting the seventh clips 7.21 over the distal side of the proximally ramped rib 9.2 one by one.

Figure 27A:
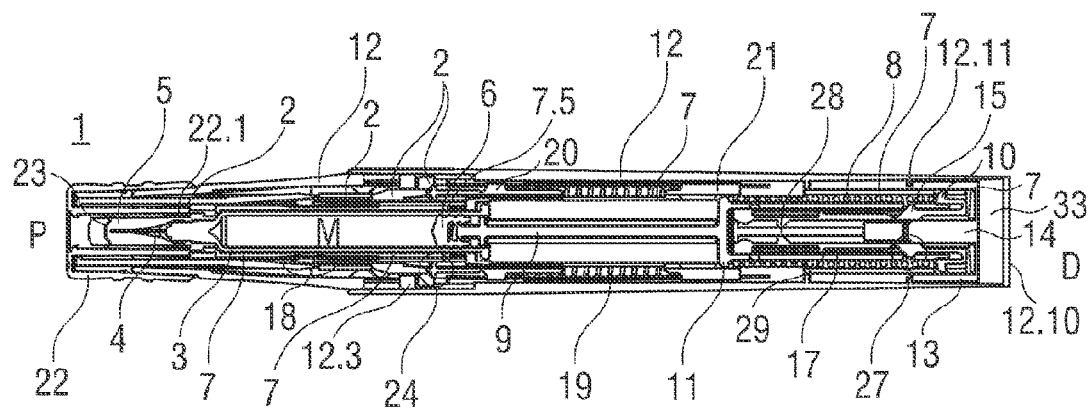
FIGS. 27A and 27B show another embodiment of the auto-injector having a wrap-over sleeve trigger instead of a trigger button.
Figure 27B:
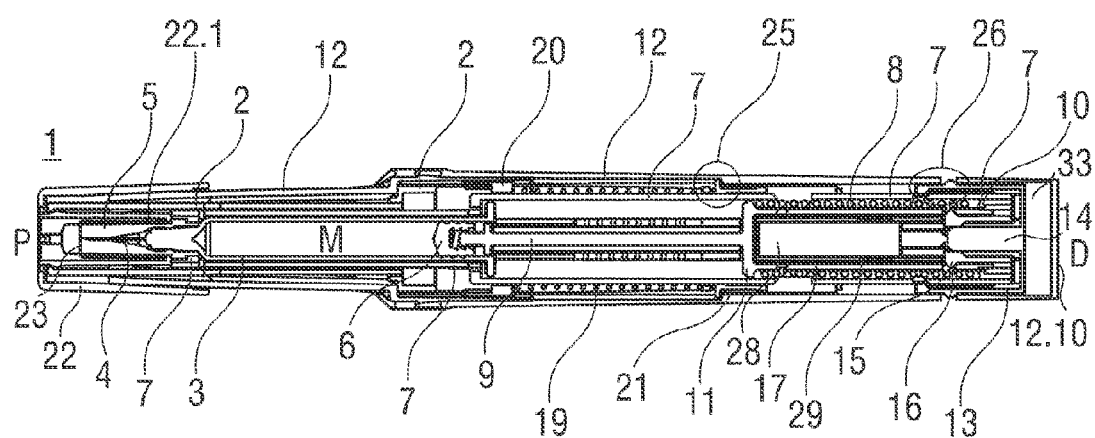

FIGS. 27A and 27B show longitudinal sections of another embodiment of the auto-injector 1 in different section planes, the different section planes approximately 90° rotated to each other, wherein the auto-injector 1 is in an initial state prior to starting an injection. The auto-injector 1 is essentially identical to the one described in FIGS. 1 to 16. However, other than the auto-injector of FIGS. 1 to 16 the auto-injector 1 of this embodiment has a wrap-over sleeve trigger instead of a trigger button.

The wrap-over sleeve trigger 12 is the same component as the case 12 which has a closed distal end face 12.10 other than the one in FIGS. 1 to 16. An internal trigger button 13 is arranged at the distal end inside the sleeve trigger 12. Other than in FIGS. 1 to 16 the trigger button 13 is not visible nor does it protrude from the case 12 in any state. In the initial state a clearance 33 is provided between the distal end face 12.10 of the sleeve trigger 12 and the internal trigger button 13 allowing for some travel of the sleeve trigger 12 without interfering with the trigger button 13.

As the auto-injector 1 does not differ from the auto-injector of FIGS. 1 to 16 in other respects it is essentially operated in the same way with the following exceptions:

As the chassis 2 is placed against the injection site the sleeve trigger 12 translates in the proximal direction P relative to the chassis 2 into the advanced position in a first phase of sleeve travel removing the clearance 33 between the distal end face 12.10 of the sleeve trigger 12 and the internal trigger button 13. As in the embodiment of FIGS. 1 to 16 this motion unlocks the detent mechanism 18 and the trigger button 13. As the user continues to depress the sleeve trigger 12 in a second phase of sleeve travel thereby further advancing it in the proximal direction P the distal end face 12.10 hits the internal trigger button 13 thereby depressing it until the first collar 20 is released from the chassis 2 and the control spring force is coupled on to the carrier 7. The carrier 7 then advances until the internal trigger button 13 stops on another rib in the case 12 and the plunger release mechanism 27 is released (note the peg 14 is shorter in this embodiment).

From a user perspective, the detent mechanism 18 is arranged to provide a resistive force when the user reaches the second phase of sleeve travel. Internally, there is no difference to the embodiment of FIGS. 1 to 16 at this point.

Needle insertion is triggered by the user fully advancing the sleeve trigger 12 in the second phase of sleeve travel thereby fully depressing the internal trigger button 13 and overcoming the detent mechanism as in the embodiment of FIGS. 1 to 16.

Figure 16C:
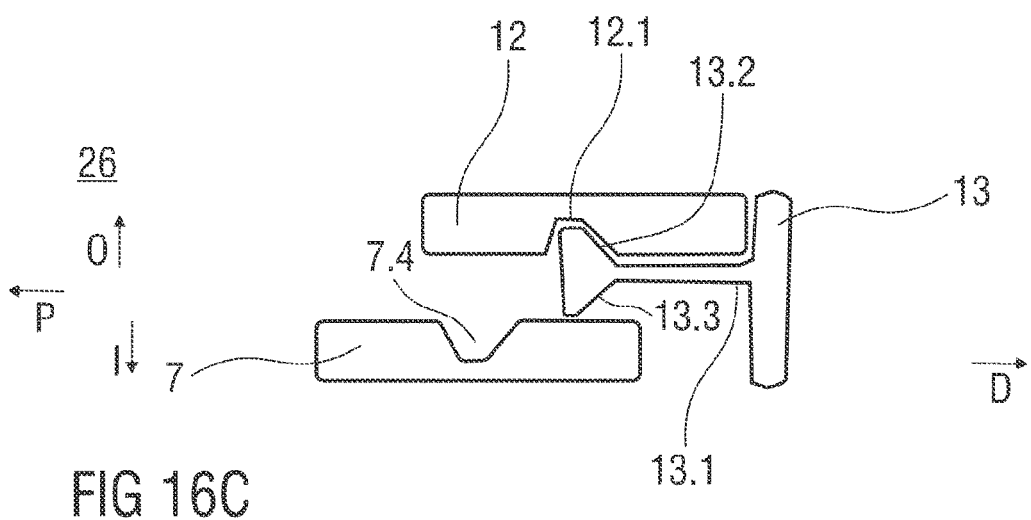

As the control spring 19 takes over on button depression fully advancing the carrier 7 for needle insertion the internal trigger button 13 bottoms out on an internal fifth rib 12.11 in the sleeve trigger 12 and the internal trigger button 13 switches back to being locked to the sleeve trigger 12 as in FIG. 16C.

The embodiment of FIGS. 27A and 27B may also be combined with the alternative features illustrated in FIGS. 17 to 26.

It goes without saying that in all ramped engagements between two components described in the above embodiments there may be just one ramp on one or the other component or there may be ramps on both components without significantly influencing the effect of the ramped engagement.

The invention claimed is:

1. An auto-injector for administering a dose of a liquid medicament (M), comprising:
a tubular chassis telescopable in a tubular case,
a carrier subassembly comprising a tubular carrier slidably arranged relative to the chassis inside the case, the carrier adapted to contain a syringe with a hollow injection needle, a drive spring and a plunger for forwarding load of the drive spring to a stopper of the syringe, wherein the syringe is lockable for joint axial translation with the carrier,
a control spring arranged around the carrier for translating the carrier in a proximal direction (P) for insertion of the needle through the chassis into an injection site,
wherein the control spring is arranged to bias the case against the chassis in a distal direction (D) so as to extend the chassis out of a proximal end (P) of the case,
wherein an insertion depth of the needle is defined by the carrier abutting the chassis in a predefined position,
wherein the case is arranged to release or allow release of the control spring for needle insertion on translation of the case in the proximal direction (P) relative to the chassis against the bias into an advanced position,
wherein a proximal end of the control spring is configured to be decoupled from the chassis and coupled to the carrier for needle insertion.

2. The auto-injector according to claim 1, wherein the carrier is arranged to be translated in the distal direction (D) for retracting the needle when the case is moved in the distal direction (D) relative to the chassis by a predefined distance.

3. The auto-injector according to claim 2, wherein the carrier is arranged to be translated in the distal direction (D) in response to the proximal end of the control spring being released from the carrier and coupled to the chassis or the case and in response to the distal end of the control spring being decoupled from the case and coupled to the carrier.

4. The auto-injector according to claim 1, wherein a trigger button is arranged distally or laterally in or on the case, wherein a needle insertion control mechanism is arranged for coupling the proximal end of the control spring to either the carrier for advancing it for needle insertion or to the chassis for needle retraction depending on a relative axial position of the carrier and the chassis, wherein a plunger release mechanism is arranged for releasing the plunger for injection when the carrier has at least almost reached an injection depth during needle insertion, wherein a detent mechanism is arranged for coupling the chassis to the carrier for joint axial translation relative to the case, wherein the detent mechanism is arranged to decouple the chassis from the carrier upon actuation of the trigger button thus allowing the carrier to move relative to the chassis so as to cause the needle insertion control mechanism to decouple the proximal end of the control spring from the chassis and couple the proximal end of the control spring to the carrier for needle insertion, wherein a syringe retraction control mechanism is arranged for coupling a distal end of the control spring to either the carrier for needle retraction or to the case otherwise.

5. The auto-injector according to claim 4, wherein the needle insertion control mechanism comprises a first collar biased by the control spring in a proximal direction (P), wherein at least one resilient beam is proximally arranged on the first collar, wherein respective recesses are arranged in the carrier and chassis, wherein a transversal extension of a head of the resilient beam is wider than a gap between the carrier and the chassis causing the head of the resilient beam to abut a distal face on the recess in the chassis while being prevented from deflecting in an inward direction (I) by the carrier or to abut a distal face on the recess in the carrier while being prevented from deflecting in an outward direction (O) by the chassis thereby forwarding load from the control spring to the carrier for needle insertion, wherein the resilient beam is arranged to be switched between the chassis and the carrier by ramped engagement of the head to the distal faces under load of the control spring depending on a relative longitudinal position between the chassis and the carrier.

6. The auto-injector according to claim 5, wherein the recess in the carrier is a first recess in the carrier, wherein the syringe retraction control mechanism comprises a second collar bearing against the distal end of the control spring and having a resilient proximal beam with a second beam head having an inward boss, wherein the second beam head is arranged to be in a ramped engagement with a case detent in the case in a manner ramping the second beam head in the inward direction (I) under load of the control spring in the distal direction (D), wherein the inward boss is arranged to inwardly abut the carrier for preventing inward deflection of the second beam head and keep the second collar locked to the case, wherein a second recess is arranged in the carrier for allowing the inward boss to be inwardly deflected on translation of the case in the distal direction (D) relative to the carrier on removal of the auto-injector from the injection site.

7. The auto-injector according to claim 5, wherein a visual use indicator is provided, comprising at least one indicator window in the case, wherein a part of the chassis is arranged to be located behind the indicator window when the case is in its distal position biased by the control spring, wherein a tab on the first collar is located outwardly from the part of the chassis after the collar has been translated in the proximal direction (P) during needle insertion, wherein the tab and the part of the chassis exhibit a visually distinctive feature.

8. The auto-injector according to claim 4, wherein the plunger release mechanism comprises at least one resilient arm on the carrier arranged to be in a ramped engagement to the plunger so as to disengage the at least one resilient arm from the plunger under load of the drive spring, wherein a peg protrudes from a distal end face of the trigger button in the proximal direction (P) in a manner to support the resilient arm preventing disengagement of the carrier from the plunger and thus release of the drive spring when the carrier is in a distal position, wherein the trigger button is arranged to remain in position relative to the case when the carrier is translated for advancing the needle so as to pull the resilient arm away from the peg thus allowing deflection of the resilient arm due to the ramped engagement under load of the drive spring for disengaging the plunger from the carrier and releasing the drive spring for drug delivery when the carrier has reached a predefined position during needle advancement.

9. The auto-injector according to claim 4, wherein the detent mechanism is arranged to provide a resistive force which has to be overcome to advance the carrier in the proximal direction (P) for needle insertion.

10. The auto-injector according to claim 9, wherein the detent mechanism comprises a resilient beam on the chassis and a rhomboid ramp member on the carrier, the resilient beam being essentially straight when relaxed and having a first beam head arranged to interact in a ramped engagement with a proximal first ramp or a distal second ramp on the rhomboid ramp member in such a manner that application of a translative force on the carrier relative to the chassis in the proximal direction (P) with the first beam head engaged to the first fourth ramp deflects the resilient beam in one transversal direction when a predetermined value of the translative force, at least depending on a resilience of the resilient beam, is overcome so as to allow the first beam head to travel along one transversal side of the rhomboid ramp member on continued relative translation of the components, wherein the resilient beam is allowed to relax when the first beam head has reached the second ramp thereby engaging it in a manner that application of a translative force on the carrier in the distal direction (D) deflects the resilient beam in another transversal direction when a predetermined value of the translative force, at least depending on the resilience of the resilient beam, is overcome so as to allow the first beam head to travel along the other transversal side of the rhomboid ramp member on continued translation of the carrier.

11. The auto-injector according to claim 4, wherein the detent mechanism is arranged to provide a resistive force resisting translation of the carrier in the distal direction (D) relative to the chassis for keeping the carrier in a defined position in a transitional state with both ends of the control spring decoupled from the carrier.

12. The auto-injector according to claim 4, wherein the case is arranged to lock the detent mechanism prior to being translated in the proximal direction (P) relative to the chassis when the chassis is being pressed against an injection site, wherein the case when translated into an advanced position in the proximal direction (P) is arranged to unlock the detent mechanism rendering it operable.

13. The auto-injector according to claim 4, wherein the trigger button is arranged distally, wherein the distally arranged trigger button is at least initially coupled to the carrier, wherein the case is arranged to abut the trigger button in the initial state preventing depression of the trigger button, wherein on translation of the case into the advanced position when the chassis is being pressed against the injection site the trigger button remains coupled to the carrier thus emerging from the case so as to allow depression for starting an injection cycle.

14. The auto-injector according to claim 4, wherein the trigger button is arranged distally, wherein the case is arranged as a wrap-over sleeve trigger having a closed distal end face covering the trigger button, wherein in an initial state a clearance is provided between the distal end face of the sleeve trigger and the trigger button allowing for some travel of the sleeve trigger against the bias of the control spring in the proximal direction (P) in a first phase before abutting the trigger button.

15. The auto-injector according to claim 4, wherein a releasable noise component is provided, capable of, upon release, generating an audible and/or tactile feedback to a user, wherein the noise component is arranged to be released when the plunger reaches a position relative to the syringe in which the stopper is located in proximity of a proximal end of the syringe, and wherein the released noise component impacts on one component of the auto-injector indicating the end of the injection.

16. The auto-injector according to claim 15, characterized in that the component of the auto-injector comprises at least part of the chassis, the case, the trigger button, the carrier, the plunger and/or a sleeve trigger.

17. The auto-injector of claim 1, further comprising:
the syringe with the hollow injection needle; and
a medicament carried in the syringe, the medicament comprising a pharmaceutically active compound.

18. The auto-injector of claim 1, wherein the proximal end of the control spring is coupled to the chassis prior to needle insertion.

* * * * *